United States Patent
Dalmau

(10) Patent No.: US 9,250,250 B2
(45) Date of Patent: Feb. 2, 2016

(54) METHODS FOR DIAGNOSING AND TREATING AN LGI1 RELATED AUTOIMMUNE DISEASE

(75) Inventor: Josep Dalmau, Delmar, NY (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 13/696,884

(22) PCT Filed: May 11, 2011

(86) PCT No.: PCT/US2011/036041
§ 371 (c)(1),
(2), (4) Date: Dec. 7, 2012

(87) PCT Pub. No.: WO2011/143298
PCT Pub. Date: Nov. 17, 2011

(65) Prior Publication Data
US 2013/0072582 A1   Mar. 21, 2013

Related U.S. Application Data

(60) Provisional application No. 61/333,453, filed on May 11, 2010.

(51) Int. Cl.
*G01N 33/68* (2006.01)
*G01N 33/564* (2006.01)
*G01N 33/574* (2006.01)

(52) U.S. Cl.
CPC .......... *G01N 33/6893* (2013.01); *G01N 33/564* (2013.01); *G01N 33/57488* (2013.01); *G01N 2800/28* (2013.01); *G01N 2800/2857* (2013.01)

(58) Field of Classification Search
None
See application file for complete search history.

(56) References Cited

U.S. PATENT DOCUMENTS

| | | | |
|---|---|---|---|
| 2009/0155261 A1 | 6/2009 | Dalmau et al. | |
| 2012/0114666 A1* | 5/2012 | Vincent | 424/172.1 |

FOREIGN PATENT DOCUMENTS

| | | |
|---|---|---|
| WO | WO 2008/021408 | 2/2008 |
| WO | WO 2010/046716 | 4/2010 |

OTHER PUBLICATIONS

Lai et al., Investigation of LGI1 as the antigen in limbic encephalitis previously attributed to potassium channels: a case series Investigation of LGI1 as the antigen in limbic encephalitis previously attributed to potassium channels: a case series, Jun. 28, 2010, Lancet Neurol 9(8):776-785.*
Ances BM et al (Treatment-responsive limbic encephalitis identified by neuropil antibodies: MRI and PET correlates. Brain 2005;128:1764-1777.
Vitaliani et al (Paraneoplastic encephalitis, psychiatric symptoms, and hypoventilation in ovarian teratoma. Ann Neurol 2005;58:594-604.
Gultekin SH et al (Paraneoplastic limbic encephalitis: neurological symptoms, immunological findings and tumour association in 50 patients. Brain 2000;123:1481-1494.
Nielson, "Peptide nucleic acids as therapeutic agents", Current Opinion in Structural Biology, 1999, 9: pp. 353-357.
Naz et al., "Novel human prostate-specific cDNA: molecular cloning, expression, and immunobiology of the recombinant protein", Biochemical and Biophysical Research Communications 297 (2002) 1075-1084.
Schulte et al., "The epilepsy linked Lgi1 protein assembles into presynaptiv kv1 channels and inhibits inactivation by kvb1", Neuron, 2006, vol. 49, pp. 697-706.
Jarius et al., "CSF findings in patients with voltage gated potassium channel antibody associated limbic encephalitis", Journal of Neurol. Sciences, 2008, vol. 268, pp. 74-77.
Barajas et al., "Adult-onset drug-refractory seizure disorder associate with anti-voltage-gated potassium-channel antibody", Epilepsia, 2009, vol. 51(3), pp. 473-477.
Antoine et al., "Limbic encephalitis and immunological perturbations in two patients with thymoma", Journal of Neurology, Neurosurgery and Psychiatry, 1995, vol. 58, pp. 706-710.
Chernova et al., Leucine-rich glioma-inactivated protein 1 precursor (epitempin 1), Uniprot direct Submission Accession No. O95970, 2003, retrieved from http://www.uniprot.org/uniprot/O95970.txt?version=13>, pp. 1-3.
Irani et al., "Antibodies to kv1 potassium channel-complex proteins leucine-rich, glioma inactivated 1 protein and contactin-associated protein-2 in limbic encephalitis, Morvans syndrome and acquired neuromyotonia", Brain, 2010, vol. 133, pp. 2734-2748.
Gu et al., "LGI1: a gene involved in epileptogenesis and glioma progression?", Neurogenetics, vol. 6, No. 2, 2005, pp. 59-66.
Lai et al., "Investigation of LGI1 as the antigen in limbic encephalitis previously attributed to potassium channels: a case series", Lancet Neurology, vol. 9, No. 8, 2010, pp. 776-785.
Caudy et al., "Fragile x-related rotein and VIG associate with the RNA interference machinery", Genes and Development 2002, 16: 2491-2496.

* cited by examiner

*Primary Examiner* — John Ulm
(74) *Attorney, Agent, or Firm* — Mark S. Cohen; Pearl Cohen Zedek Latzer Baratz LLP

(57) ABSTRACT

The invention provides methods of diagnosing or determining a cause of an autoimmune encephalitis or an epilepsy in a subject and of diagnosing a tumor in a subject, comprising the step of testing a biological sample of the subject for an antibody to LGI1. This invention further provides methods of treating an autoimmune encephalitis or an epilepsy, comprising the steps of detecting an antibody to LGI1 and treating a tumor associated with the disease.

4 Claims, 7 Drawing Sheets

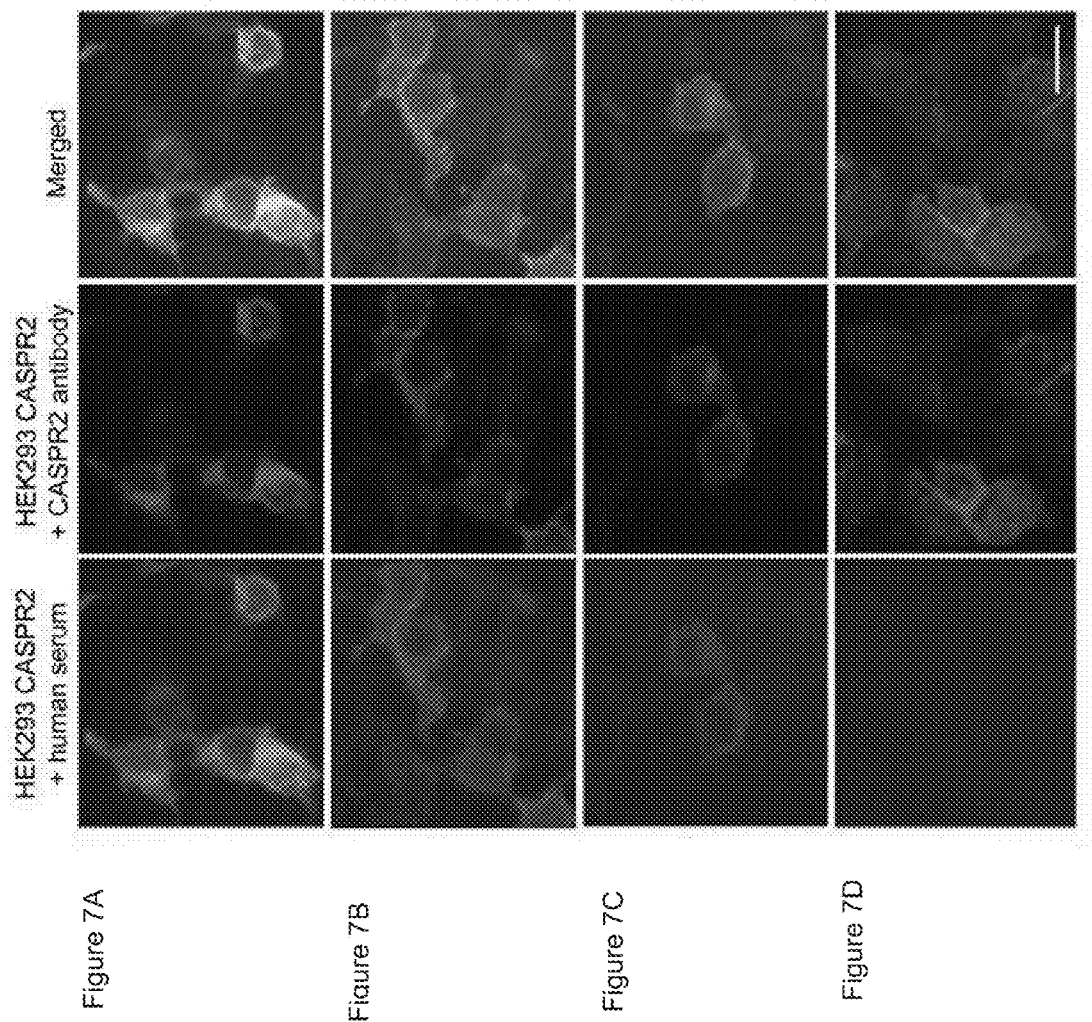

SEQUENCE LISTING

```
<160> NUMBER OF SEQ ID NOS: 10

<210> SEQ ID NO 1
<211> LENGTH: 2366
<212> TYPE: DNA
<213> ORGANISM: Homo sapiens

<400> SEQUENCE: 1
gaaagcagaa agctgtttat tttctgtgac atcacttcac tttgccttcg aaggctggtc      60
```

```
tgtgctcagt gttttcgtgg tgatgcaagt cggctctctc ctccagcagt tggatccctc    120
ccatctcaca gtacctcaca ggtctcttcc cccgagcagt gcattgctgg agcgaggaga    180
agctcacgaa tcagctgcag gtctctgttt tgaaaaagca gagatacaga ggcagaggaa    240
aagggtggac tcctatgtga cctgttctta gagcaagaca atcaccatct gaattccaga    300
agccctgttc atggttgggg atattttctc gactgcatgg aatcagaaag aagcaaaagg    360
atgggaaatg cctgcattcc cctgaaaaga attgcttatt ccctatgtct cttatctgcg    420
cttttgctga ctgaggggaa gaaaccagcg aagccaaaat gccctgccgt gtgtacttgt    480
accaaagata atgctttatg tgagaatgcc agatccattc cacgcaccgt tcctcctgat    540
gttatctcat tatcctttgt gagatctggt tttactgaaa tctcagaagg gagtttttta    600
ttcacgccat cgctgcagct cttgttattc acatcgaact cctttgatgt gatcagtgat    660
gatgctttta ttggtcttcc acatctagag tatttattca tagaaaacaa caacatcaag    720
tcaatttcaa gacatacttt ccggggacta aagtcattaa ttcacttgag ccttgcaaac    780
aacaatctcc agacactccc aaaagatatt ttcaaaggcc tggattcttt aacaaatgtg    840
gacctgaggg gtaattcatt taattgtgac tgtaaactga atggctagt ggaatggctt     900 ggccacacca atgcaactgt tgaagacatc tactgcgaag ccccccaga atacaagaag     960 cgcaaaatca atagtctctc ctcgaaggat ttcgattgca tcattacaga atttgcaaag    1020
tctcaagacc tgccttatca atcattgtcc atagacactt tttcttattt gaatgatgag    1080
tatgtagtca tcgctcagcc ttttactgga aaatgcattt tccttgaatg ggaccatgtg    1140
gaaaagacct tccggaatta tgacaacatt acaggcacat ccactgtagt atgcaagcct    1200
atagtcattg aaactcagct ctatgttatt gtggcccagc tgtttggtgg ctctcacatc    1260
tataagcgag acagttttgc aaataaattc ataaaaatcc aggatattga aattctcaaa    1320
atccgaaaac ccaatgacat tgaaacattc aagattgaaa acaactggta ctttgttgtt    1380
gctgacagtt caaaagctgg ttttactacc atttacaaat ggaacggaaa cggattctac    1440
tcccatcaat ccttcacgc gtggtacagg gacactgatg tggaatatct agaaatagtc    1500
agaacacctc agacactcag aacgcctcat ttaattctgt ctagtagttc ccagcgtcct    1560
gtaatttatc agtggaacaa agcaacacaa ttattcacta accaaactga cattcctaac    1620
atggaggatg tgtacgcagt gaagcacttc tcagtgaaag gggacgtgta catttgcttg    1680
acaagattca ttggtgattc caaagtcatg aaatggggag ctcctcgtt ccaggatatt     1740 cagaggatgc catcgcgagg atccatggtg ttccagcctc tcaaataaa taattaccaa    1800 tatgcaattc ttggaagtga ttactccttt actcaagtgt ataactggga tgcagagaaa    1860
gccaaatttg tgaaatttca ggaattaaat gttcaggcac aagatcatt cacacatgtg     1920 tccattaata agcgtaattt tctttttgct tccagtttta agggaaatac acagatttac    1980
aaacatgtca tagttgactt aagcgcatga gacaccaaat tctgtggctg ccatcagaaa    2040
ttttctacag tacatgaccc ggatgaactc aatgcatgat gactcttctt atcacacttg    2100
caaatgaatg cctttcaaac attgagactg ctagaaccaa gcactaccag tatctccatc    2160
cttaactgtc cagtccagtg atgtgggaag ttacctttta taagacaaaa tttaattgtg    2220
taactgttct ttgcagtgaa gatgtgtaaa taagcgttta atggtatctg ttactccaaa    2280
aagaaatatt aatatgtact tttccatttta tttattcatg tgtacagaaa caactgccaa    2340
ataaaatgtt tacattttct ttcata                                         2366
```

<210> SEQ ID NO 2
<211> LENGTH: 557
<212> TYPE: PRT
<213> ORGANISM: Homo sapiens

<400> SEQUENCE: 2

Met Glu Ser Glu Arg Ser Lys Arg Met Gly Asn Ala Cys Ile Pro Leu
1               5                   10                  15

Lys Arg Ile Ala Tyr Phe Leu Cys Leu Leu Ser Ala Leu Leu Leu Thr
            20                  25                  30

Glu Gly Lys Lys Pro Ala Lys Pro Lys Cys Pro Ala Val Cys Thr Cys
        35                  40                  45

Thr Lys Asp Asn Ala Leu Cys Glu Asn Ala Arg Ser Ile Pro Arg Thr
50                  55                  60

Val Pro Pro Asp Val Ile Ser Leu Ser Phe Val Arg Ser Gly Phe Thr
65                  70                  75                  80

Glu Ile Ser Glu Gly Ser Phe Leu Phe Thr Pro Ser Leu Gln Leu Leu
                85                  90                  95

Leu Phe Thr Ser Asn Ser Phe Asp Val Ile Ser Asp Asp Ala Phe Ile
                100                 105                 110

Gly Leu Pro His Leu Glu Tyr Leu Phe Ile Glu Asn Asn Ile Lys
            115                 120                 125

Ser Ile Ser Arg His Thr Phe Arg Gly Leu Lys Ser Leu Ile His Leu
130                 135                 140

Ser Leu Ala Asn Asn Asn Leu Gln Thr Leu Pro Lys Asp Ile Phe Lys
145                 150                 155                 160

Gly Leu Asp Ser Leu Thr Asn Val Asp Leu Arg Gly Asn Ser Phe Asn
                165                 170                 175

Cys Asp Cys Lys Leu Lys Trp Leu Val Glu Trp Leu Gly His Thr Asn
                180                 185                 190

Ala Thr Val Glu Asp Ile Tyr Cys Glu Gly Pro Pro Glu Tyr Lys Lys
            195                 200                 205

Arg Lys Ile Asn Ser Leu Ser Ser Lys Asp Phe Asp Cys Ile Ile Thr
210                 215                 220

Glu Phe Ala Lys Ser Gln Asp Leu Pro Tyr Gln Ser Leu Ser Ile Asp
225                 230                 235                 240

Thr Phe Ser Tyr Leu Asn Asp Glu Tyr Val Val Ile Ala Gln Pro Phe
                245                 250                 255

Thr Gly Lys Cys Ile Phe Leu Gly Trp Asp His Val Glu Lys Thr Phe
            260                 265                 270

Arg Asn Tyr Asp Asn Ile Thr Gly Thr Ser Thr Val Val Cys Lys Pro
275                 280                 285

Ile Val Ile Glu Thr Gln Leu Tyr Val Ile Val Ala Gln Leu Phe Gly
            290                 295                 300

Gly Ser His Ile Tyr Lys Arg Asp Ser Phe Ala Asn Lys Phe Ile Lys
305                 310                 315                 320

Ile Gln Asp Ile Glu Ile Leu Lys Ile Arg Lys Pro Asn Asp Ile Glu
                325                 330                 335

Thr Phe Lys Ile Glu Asn Asn Trp Tyr Phe Val Val Ala Asp Ser Ser
            340                 345                 350

Lys Ala Gly Phe Thr Thr Ile Tyr Lys Trp Asn Gly Asn Gly Phe Tyr
            355                 360                 365

Ser His Gln Ser Leu His Ala Trp Tyr Arg Asp Thr Asp Val Glu Tyr
370                 375                 380

```
Leu Glu Ile Val Arg Thr Pro Gln Thr Leu Arg Thr Pro His Leu Ile
385                 390                 395                 400

Leu Ser Ser Ser Gln Arg Pro Val Ile Tyr Gln Trp Asn Lys Ala
            405                 410                 415

Thr Gln Leu Phe Thr Asn Gln Thr Asp Ile Pro Asn Met Glu Asp Val
            420                 425                 430

Tyr Ala Val Lys His Phe Ser Val Lys Gly Asp Val Tyr Ile Cys Leu
            435                 440                 445

Thr Arg Phe Ile Gly Asp Ser Lys Val Met Lys Trp Gly Gly Ser Ser
            450                 455                 460

Phe Gln Asp Ile Gln Arg Met Pro Ser Arg Gly Ser Met Val Phe Gln
465                 470                 475                 480

Pro Leu Gln Ile Asn Asn Tyr Gln Tyr Ala Ile Leu Gly Ser Asp Tyr
            485                 490                 495

Ser Phe Thr Gln Val Tyr Asn Trp Asp Ala Glu Lys Ala Lys Phe Val
            500                 505                 510

Lys Phe Gln Glu Leu Asn Val Gln Ala Pro Arg Ser Phe Thr His Val
            515                 520                 525

Ser Ile Asn Lys Arg Asn Phe Leu Phe Ala Ser Ser Phe Lys Gly Asn
            530                 535                 540

Thr Gln Ile Tyr Lys His Val Ile Val Asp Leu Ser Ala
545                 550                 555

<210> SEQ ID NO 3
<211> LENGTH: 10
<212> TYPE: PRT
<213> ORGANISM: Homo sapiens

<400> SEQUENCE: 3

Lys Ala Gly Phe Thr Thr Ile Tyr Lys Trp
1               5                   10

<210> SEQ ID NO 4
<211> LENGTH: 10
<212> TYPE: PRT
<213> ORGANISM: Homo sapiens

<400> SEQUENCE: 4

Lys Ile Gln Asp Ile Glu Val Leu Lys Ile
1               5                   10

<210> SEQ ID NO 5
<211> LENGTH: 12
<212> TYPE: PRT
<213> ORGANISM: Homo sapiens

<400> SEQUENCE: 5

Lys Phe Gln Glu Leu Asn Val Gln Ala Pro Arg Ser
1               5                   10

<210> SEQ ID NO 6
```

```
<211> LENGTH: 13
<212> TYPE: PRT
<213> ORGANISM: Homo sapiens

<400> SEQUENCE: 6

Lys Gly Leu Asp Ser Leu Thr Asn Val Asp Leu Arg Gly
1               5                   10

<210> SEQ ID NO 7
<211> LENGTH: 13
<212> TYPE: PRT
<213> ORGANISM: Homo sapiens

<400> SEQUENCE: 7

Lys Trp Gly Gly Ser Ser Phe Gln Asp Ile Gln Arg Met
1               5                   10

<210> SEQ ID NO 8
<211> LENGTH: 10
<212> TYPE: PRT
<213> ORGANISM: Rattus norvegicus

<400> SEQUENCE: 8

Arg Thr Asn Ser Pro Leu Gln Val Lys Thr
1               5                   10

<210> SEQ ID NO 9
<211> LENGTH: 9
<212> TYPE: PRT
<213> ORGANISM: Rattus norvegicus

<400> SEQUENCE: 9

Met Leu Tyr Ser Asp Thr Gly Arg Asn
1               5

<210> SEQ ID NO 10
<211> LENGTH: 12
<212> TYPE: PRT
<213> ORGANISM: Rattus norvegicus

<400> SEQUENCE: 10

Arg His Asp Leu Gln His Ala Val Val Ala Arg Tyr
1               5                   10
```

METHODS FOR DIAGNOSING AND TREATING AN LGI1 RELATED AUTOIMMUNE DISEASE

CROSS-REFERENCE TO RELATED APPLICATIONS

This application is a National Phase Application of PCT International Application No. PCT/US11/36041, International Filing Date May 11, 2011, claiming priority to U.S. Provisional Patent Application 61/333,453, filed May 11, 2010, each of which is incorporated by reference herein in its entirety.

FIELD OF THE INVENTION

The invention relates to methods for diagnosing and treating an autoimmune encephalitis or an epilepsy in a subject using an antibody to leucine-rich glioma inactivated 1 (LGI1).

BACKGROUND OF THE INVENTION

Limbic encephalitis is a serious neurological disease that causes inflammation in brain limbic system, including hippocampus, thalamus, hypothalamus, and amygdale. Patients with limbic encephalitis often present with memory loss, seizures and/or confusion.

Encephalitis, including limbic encephalitis, fall into two main categories: infectious encephalitis—caused by direct invasion of the brain by an infectious agent, usually a virus and autoimmune encephalitis—caused by the persons own immune system reacting against itself.

Autoimmune limbic encephalitis can be either paraneoplastic limbic encephalitis (PLE) or non-paraneoplastic limbic encephalitis (NPLE). Until the mid-1990s, most cases of non-viral limbic encephalitis were considered to be paraneoplastic.

Paraneoplastic limbic encephalitis (PLE) occurs in a small proportion of people with particular cancers. Most individuals with PLE will turn out to have a cancer in lung, thymus gland, breast or testis. In many cases, PLE can be diagnosed by testing for one of a group of paraneoplastic autoantibodies in blood. The condition may improve or at least stabilise if the cancer is detected and treated effectively.

NPLE has been attributed in many cases to specific antibodies in blood that target the potassium channel, called voltage-gated potassium channel (VGKC) antibody-associated encephalitis. This type of NPLE is believed to cause a reduction in the number of potassium channels, decreasing the control over neuronal synaptic transmission.

An accurate diagnosis of autoimmune encephalitis is particularly important because the disease is potentially treatable, using immunosuppressive drugs such as steroids. A cell based assay in which HEK293 cells transfected with autoantigen serve as a substrate for an unambiguous immunocytochemical assay for antibody detection in patients' serum or CSF is needed. Over the years, multiple attempts to develop an assay where cells transfected with Kv subunits of the VGKC have failed. Currently, VGKC antibody-associated encephalitis is diagnosed using immunoprecipitation techniques based on $^{125}$I-α-dendrotoxin-labeled VGKC (dendrotoxin binds to Kv1.1, Kv1.2 and Kv1.6). This test however, is neither accurate nor specific. Accordingly, there exists a need for improved methods of diagnosing and treating autoimmune encephalitis or epileptic seizures.

SUMMARY OF THE INVENTION

In one embodiment, the present invention provides a method for diagnosing an encephalitis in a subject, comprising the steps of: obtaining a biological sample from said subject; and testing said biological sample to determine the presence of an antibody to LGI1, whereby the presence of said antibody in said biological sample indicates an autoimmune encephalitis, thereby diagnosing said encephalitis in said subject.

In another embodiment, the present invention provides a method for diagnosing an occult tumor associated with an autoimmune encephalitis in a subject, comprising the steps of: obtaining a biological sample from said subject; and testing said biological sample to determine the presence of an antibody to LGI1, whereby the presence of said antibody in said biological sample indicates the presence of said occult tumor in said subject and that said tumor is a cause of said autoimmune encephalitis.

In another embodiment, the present invention provides a method for diagnosing an epilepsy in a subject, comprising the steps of: obtaining a biological sample from said subject; and testing said biological sample to determine the presence of an antibody to LGI1, whereby the presence of said antibody in said biological sample indicates the presence of a tumor in said subject and said tumor is a cause of said epilepsy, thereby diagnosing said epilepsy in said subject.

In another embodiment, the present invention provides a method for diagnosing a tumor in a subject having an epilepsy, comprising the step of: obtaining a biological sample from said subject; and testing said biological sample to determine the presence of an antibody to LGI1, whereby the presence of said antibody in said biological sample indicates the presence of a tumor in said subject, thereby diagnosing said tumor in said subject having said epilepsy.

In another embodiment, the present invention provides a method for treating an autoimmune encephalitis in a subject, comprising the steps of: detecting a tumor associated with said autoimmune encephalitis by testing a body fluid from said subject for an antibody to LGI1, whereby the presence of said antibody in said body fluid indicates the presence of said tumor in said subject and that said tumor is a cause of said autoimmune encephalitis; and treating said tumor.

In another embodiment, the present invention provides a method for detecting an antibody to LGI1, whereby the detection of said antibody leads to treatment of an epilepsy or encephalitis with immunotherapy.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

FIG. 2: (A) Reactivity of patients' antibodies with HEK293 cells expressing LGI1 alone or associated with its receptors, ADAM22 and ADAM23. HEK293 cells expressing the indicated proteins, immunostained with patient's serum (top row), commercial antibodies against LGI1 (first column), HA-tag (columns 2-5, HA-tag present in ADAM22 an ADAM23) and Kv1.1 (last column). Merged reactivities are shown in the bottom row in a. Patient's antibodies specifically recognized LGI1 expressed alone or co-expressed with its receptors ADAM22 or ADAM23. The co-localization of reactivities is seen when LGI1 is co-expressed with ADAM22 or ADAM23. Similar studies using a control serum sample are shown in B. Scale bar=20 µm.

Figure 3:
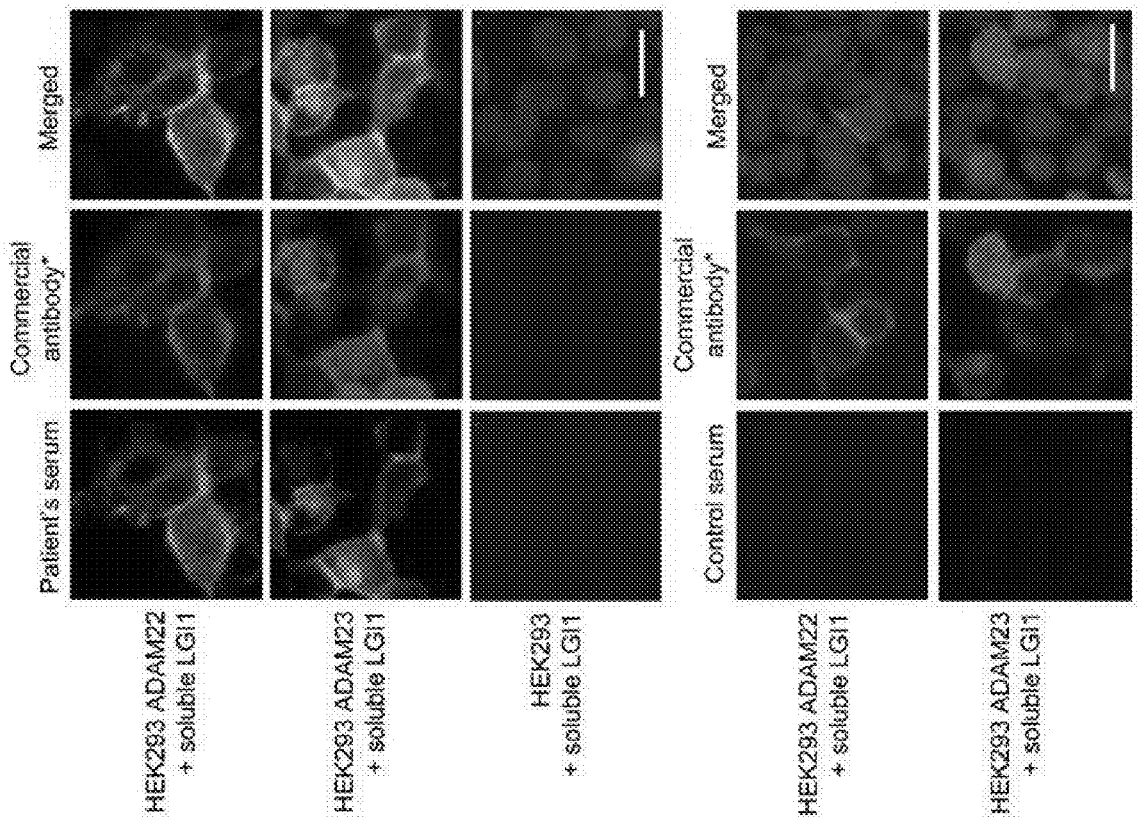

FIG. 3: Reactivity of patients' antibodies with soluble LGI1 bound to ADAM22 or ADAM23. HEK293 cells expressing ADAM22 or ADAM23 were treated with media containing soluble LGI1, and subsequently with patient's serum. Patient's antibodies recognize LGI1 bound to ADAM22 or ADAM23 (first and second rows), but not HEK293 cells without expression of these receptors (third row). The fourth and fifth rows show lack of reactivity of a control serum. Scale bar=20 µm.

Figures 4A, 4B:
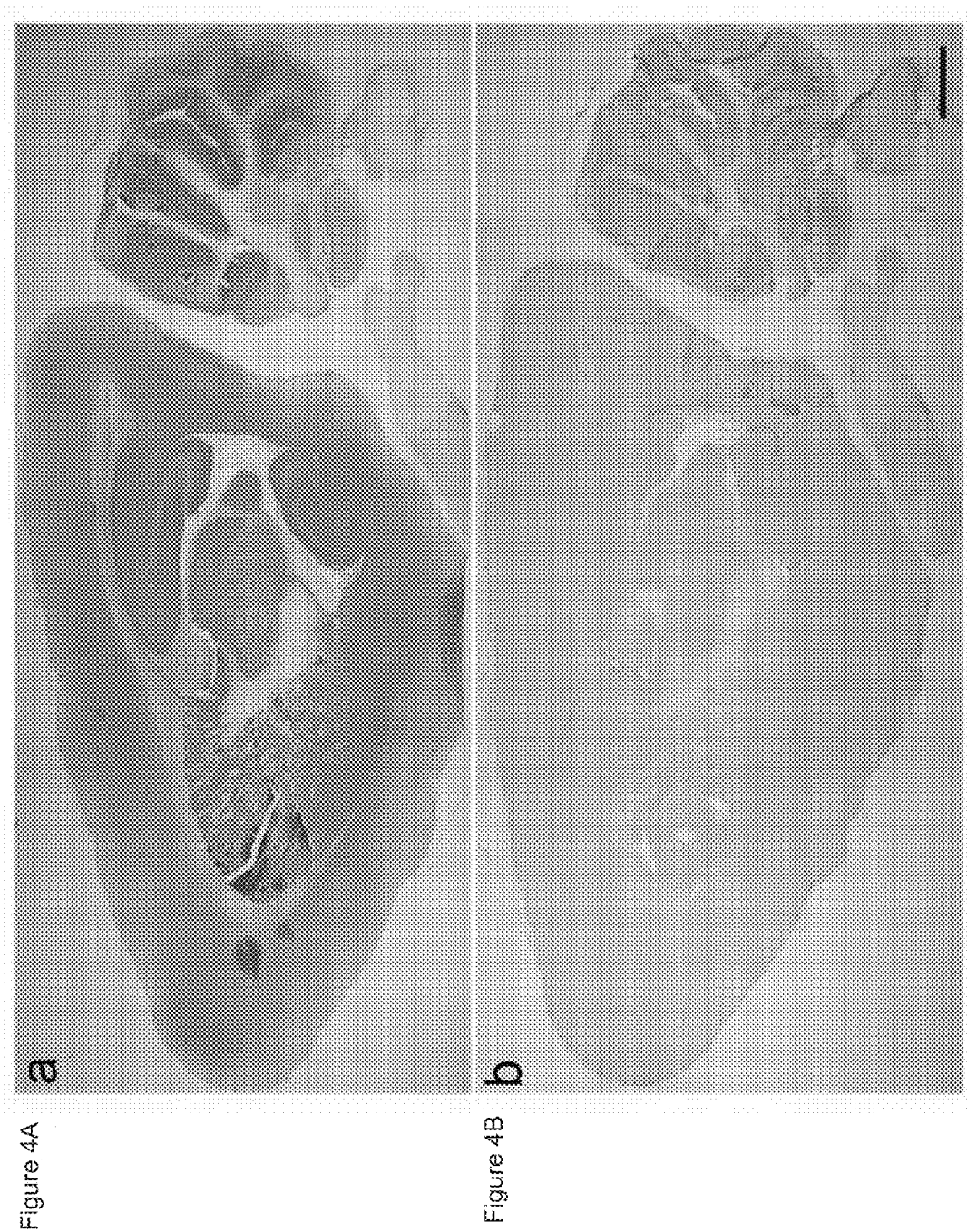

FIG. 4: Immunoabsorption of patient's serum with LGI1 abrogates reactivity with rat brain. Rat brain immunostained with serum of a patient with limbic encephalitis and antibodies attributed to VGKC, before (A) and after (B) immunoabsorption with LGI1. Scale bar=300 µm.

Figure 5:
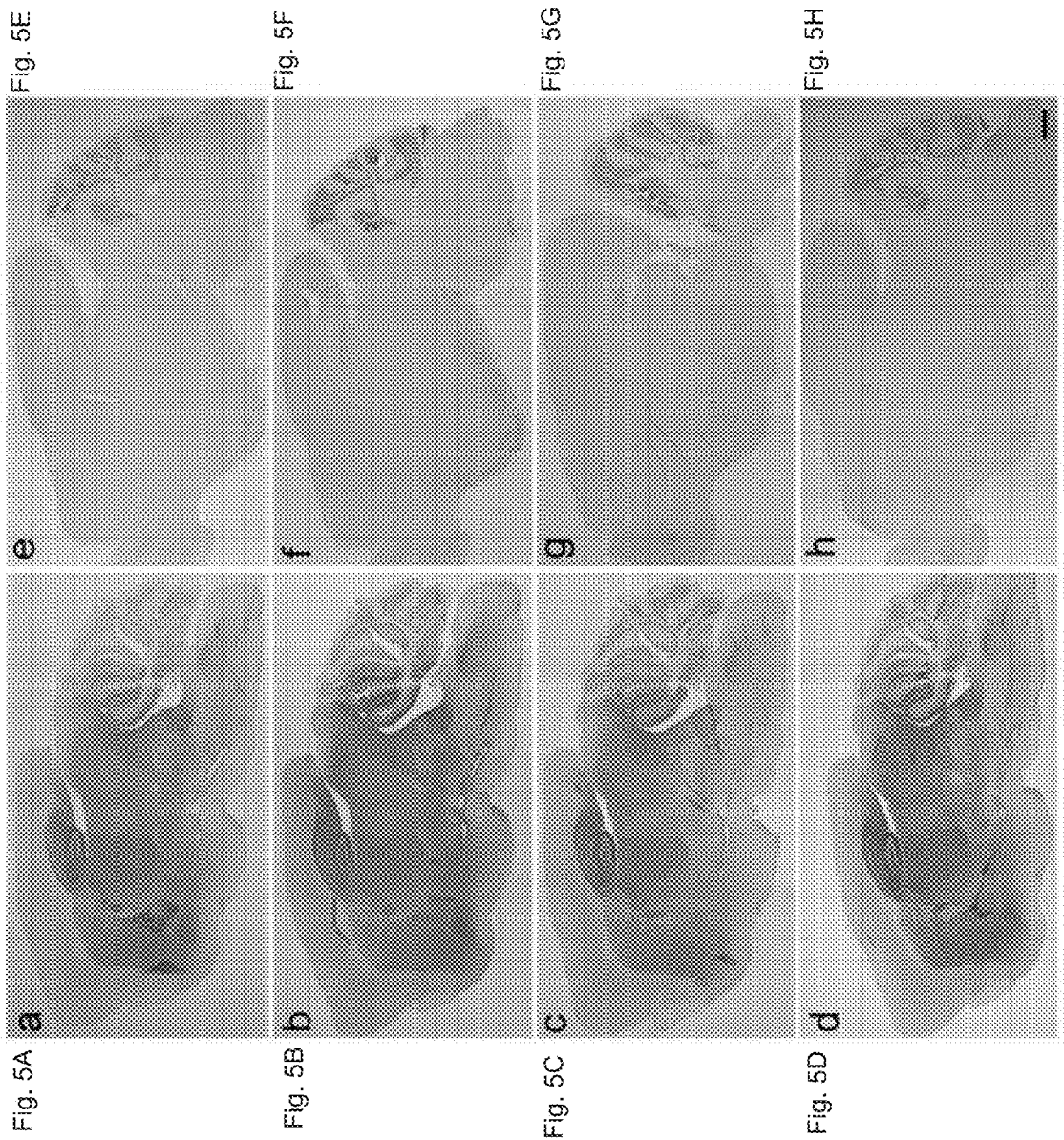

FIG. 5: Lack of reactivity of patients' antibodies with brain of Lgi1-null mice. Sections of brain of wild-type (A-D) and Lgi-null mice (E-H) incubated with serum of 4 patients with limbic encephalitis and antibodies attributed to VGKC. The lack of reactivity of patients' antibodies with brain of Lgi-null mice was noticed. Scale bar=500 µm FIG. 6: Expression of Kv1.1 by brain of Lgi1-null mice. Immunoblots of hippocampal protein extracts (50 µg/lane) from brain of wild-type and Lgi1-null mice probed with a rabbit antibody against LGI1 (dilution 1:500, top lanes) and a mouse monoclonal antibody against Kv1.1 (bottom lanes). The expression of Kv1.1 is preserved in Lgi1-null mice.

FIG. 7: Patients' sera positive by $^{125}$I-α-dendrotoxin RIA, but without LGI1 antibodies, react with CASPR2. HEK293 cells expressing CASPR2 immunostained with human sera (left column) from a patient with severe encephalitis and seizures (A), a patient with neuromyotonia (B), a patient with Morvan's syndrome (C), and a normal individual (D). The middle column shows the corresponding reactivity with a rabbit antibody against CASPR2, and the last column shows the merged reactivities. All 3 patients' sera, but not the control, react with cells expressing CASPR2. Scale bar=20 µm.

DETAILED DESCRIPTION OF THE INVENTION

The invention relates to methods for diagnosing and treating an autoimmune encephalitis or an epilepsy in a subject using an antibody to LGI1.

In one embodiment, provided herein is a method for diagnosing an encephalitis in a subject, comprising the steps of: obtaining a biological sample from said subject; and testing said biological sample to determine the presence of an antibody to LGI1, whereby the presence of said antibody in said biological sample indicates an autoimmune encephalitis, thereby diagnosing said encephalitis in said subject. In another embodiment, provided herein is a method for diagnosing a tumor associated with an autoimmune encephalitis in a subject, comprising the steps of: obtaining a biological sample from said subject; and testing said biological sample to determine the presence of an antibody to LGI1, whereby the presence of said antibody in said biological sample indicates the presence of an occult tumor in said subject and that said tumor is a cause of said autoimmune encephalitis.

In another embodiment, provided herein is a method for diagnosing epilepsy in a subject, comprising the steps of: obtaining a biological sample from said subject; and testing said biological sample to determine the presence of an antibody to LGI1, whereby the presence of said antibody in said biological sample indicates the presence of a tumor in said subject and said tumor is a cause of said epilepsy, thereby diagnosing said epilepsy in said subject. In another embodiment, provided herein is a method for diagnosing a tumor in a subject having an epilepsy, comprising the step of: obtaining a biological sample from said subject; and testing said biological sample to determine the presence of an antibody to LGI1, whereby the presence of said antibody in said biological sample indicates the presence of a tumor in said subject, thereby diagnosing said tumor in said subject having said epilepsy.

In another embodiment, provided herein is a method for treating an autoimmune encephalitis in a subject, comprising the steps of: detecting a tumor associated with said autoimmune encephalitis by testing a body fluid from said subject for an antibody to LGI1, whereby the presence of said antibody in said body fluid indicates the presence of said tumor in said subject and that said tumor is a cause of said autoimmune encephalitis; and treating said tumor.

In one embodiment, the present invention provides a method of determining a cause of an encephalitis in a subject, comprising the step of testing a body fluid of the subject for an antibody to LGI1, thereby determining a cause of an encephalitis in a subject. In another embodiment, the presence of an antibody to an epitope of LGI1 in the body fluid indicates that the encephalitis is of autoimmune etiology. In another embodiment, the presence of an antibody to a functional domain (e.g., Epilepsy Associated Repeat domain) of LGI1 in the body fluid indicates that the encephalitis is of autoimmune etiology. Each possibility represents a separate embodiment of the present invention.

In another embodiment, the methods and compositions provided herein facilitate the recognition of a severe form of autoimmune encephalitis that is often responsive to treatment. In another embodiment, the methods and compositions described herein emphasize the idea that autoimmunity can affect behavior, and particularly that an antibody to LGI1 may alter emotion, in one embodiment, or memory, consciousness or their combination in other independent embodiments.

In another embodiment, the present invention provides a method of determining a cause of an autoimmune encephalitis in a subject, comprising the step of testing a body fluid of the subject for an antibody to LGI1, thereby determining a cause of an autoimmune encephalitis in a subject. In another embodiment, the presence of the antibody indicates the presence of a tumor in the subject. In another embodiment, the tumor is a cause of the autoimmune encephalitis. Each possibility represents a separate embodiment of the present invention.

In another embodiment, the present invention provides a method of diagnosing an autoimmune encephalitis in a subject, comprising the step of testing a body fluid of the subject for an antibody to a functional domain of LGI1, thereby diagnosing said autoimmune encephalitis in said subject.

The biological sample used in the methods described herein is a body fluid that is tested by methods of the present invention is, in another embodiment, a cerebro-spinal fluid (CSF). In another embodiment, the body fluid is plasma. In another embodiment, the body fluid is any other type of fluid known in the art. Each possibility represents a separate embodiment of the present invention. In another embodiment, the biological sample is, blood, sera, or their combination in another embodiment.

The encephalitis of methods and compositions of the present invention is, in another embodiment, an autoimmune encephalitis. In one embodiment, the autoimmune encephalitis is a paraneoplastic encephalitis. In another embodiment, the autoimmune encephalitis is a non-paraneoplastic encephalitis. In another embodiment, the autoimmune encephalitis is a paraneoplastic autoimmune encephalitis. In another embodiment, the autoimmune encephalitis is a non-paraneoplastic, autoimmune encephalitis. In another embodiment, the autoimmune encephalitis is any other type of autoimmune encephalitis known in the art. Each possibility represents a separate embodiment of the present invention.

In one embodiment, the frequency of paraneoplastic anti-LGI1 encephalitis, diagnosed by the methods described herein, is unknown. In another embodiment paraneoplastic anti-LGI1 encephalitis is frequently unrecognized. This may be due to several features that make this disorder unique among paraneoplastic encephalitis, including in one embodiment, short-term memory loss or, in another embodiment, the unusual presentation with prominent psychiatric manifestations, or in another embodiment, normal or abnormal MRI findings, which in 75% of cases consist of increased T2 or FLAIR signal in the medial temporal lobes, or in yet another embodiment, the presence of tumors of the thymus or lung. In one embodiment, any of the subjects presenting the symptoms described hereinabove are diagnosed using the methods described herein.

In another embodiment, the autoimmune encephalitis is a limbic encephalitis. In another embodiment, the autoimmune encephalitis is associated with a limbic dysfunction. In another embodiment, the autoimmune encephalitis is not associated with a limbic dysfunction. Each possibility represents a separate embodiment of the present invention.

In one embodiment, limbic encephalitis causes impressive deficits that are characteristically dominated by rapid and severe loss of short-term memory. In another embodiment, patients show subacute encephalitis of later adult life, mainly affecting the limbic areas with evidence of cancer in one embodiment. In one embodiment, the term "limbic encephalitis" refers to a subject exhibiting severe short-term memory loss and dementia in association with tumors of the thymus or lung cancer.

In another embodiment, the autoimmune encephalitis of methods and compositions of the present invention is associated with seizures. In another embodiment, the autoimmune encephalitis is associated with dementia. In another embodiment, the autoimmune encephalitis is associated with a psychiatric symptom. In another embodiment, the autoimmune encephalitis is associated with an abnormality in cognition. In another embodiment, the autoimmune encephalitis is associated with an abnormality in behavior.

In another embodiment, the autoimmune encephalitis is associated with amnesia. In another embodiment, the autoimmune encephalitis is associated with a memory deficit. In another embodiment, the autoimmune encephalitis is associated with memory problems. In another embodiment, the autoimmune encephalitis is associated with a syndrome resembling Jakob-Creutfeld.

In another embodiment, the autoimmune encephalitis is associated with a decreased level of consciousness.

In another embodiment, the autoimmune encephalitis is associated with, dysfunction of any part of the brain or spinal cord. In another embodiment, the autoimmune encephalitis is associated with a combination of any of the above symptoms or disorders. Each type of encephalitis represents a separate embodiment of the present invention.

In one embodiment, the autoimmune encephalitis is associated with a tumor. In one embodiment, the tumor is a tumor of the lung or tumor of the thymus. In another embodiment, the tumor is a thymic tumor.

In another embodiment, the tumor is a testicular tumor. In another embodiment, the cancer associated with the encephalitis is a cervical cancer tumor. In another embodiment, the cancer is a head and neck cancer tumor. In another embodiment, the cancer is a breast cancer tumor. In another embodiment, the cancer is an ano-genital cancer tumor.

In another embodiment, the cancer is a melanoma. In another embodiment, the cancer is a sarcoma. In another embodiment, the cancer is a carcinoma. In another embodiment, the cancer is a lymphoma. In another embodiment, the cancer is a leukemia. In another embodiment, the cancer is a mesothelioma. In another embodiment, the cancer is a glioma. In another embodiment, the cancer is a germ cell tumor. In another embodiment, the cancer is a choriocarcinoma. Each possibility represents a separate embodiment of the present invention.

In another embodiment, the cancer is pancreatic cancer. In another embodiment, the cancer is ovarian cancer. In another embodiment, the cancer is gastric cancer. In another embodiment, the cancer is a carcinomatous lesion of the pancreas. In another embodiment, the cancer is pulmonary adenocarcinoma. In another embodiment, the cancer is colorectal adenocarcinoma. In another embodiment, the cancer is pulmonary squamous adenocarcinoma. In another embodiment, the cancer is gastric adenocarcinoma. In another embodiment, the cancer is an ovarian surface epithelial neoplasm (e.g. a benign, proliferative or malignant variety thereof). In another embodiment, the cancer is an oral squamous cell carcinoma. In another embodiment, the cancer is non small-cell lung carcinoma. In another embodiment, the cancer is an endometrial carcinoma. In another embodiment, the cancer is a bladder cancer. In another embodiment, the cancer is a head and neck cancer. In another embodiment, the cancer is a prostate carcinoma.

In another embodiment, the cancer is an acute myelogenous leukemia (AML). In another embodiment, the cancer is a myelodysplastic syndrome (MDS). In another embodiment, the cancer is a non-small cell lung cancer (NSCLC). In another embodiment, the cancer is a Wilms' tumor. In another embodiment, the cancer is a leukemia. In another embodiment, the cancer is a lymphoma. In another embodiment, the cancer is a desmoplastic small round cell tumor. In another embodiment, the cancer is a mesothelioma (e.g. malignant mesothelioma). In another embodiment, the cancer is a gastric cancer. In another embodiment, the cancer is a colon cancer. In another embodiment, the cancer is a lung cancer. In another embodiment, the cancer is a breast cancer. In another embodiment, the cancer is a germ cell tumor. In another embodiment, the cancer is an ovarian cancer. In another embodiment, the cancer is a uterine cancer. In another embodiment, the cancer is a thyroid cancer. In another embodiment, the cancer is a hepatocellular carcinoma. In another embodiment, the cancer is a thyroid cancer. In another embodiment, the cancer is a liver cancer. In another embodiment, the cancer is a renal cancer. In another embodiment, the cancer is a kaposis. In another embodiment, the cancer is a sarcoma. In another embodiment, the cancer is another carcinoma or sarcoma.

In another embodiment, the tumor is any other type of tumor known in the art. Each possibility represents a separate embodiment of the present invention.

In another embodiment, the present invention provides a method of determining a cause of an epilepsy in a subject, comprising the step of testing a body fluid of said subject for an antibody to LGI1, thereby determining a cause of said epilepsy in said subject. In another embodiment, the antibody indicates a presence of a tumor in the subject. In another embodiment, the tumor is a cause of the epilepsy. Each possibility represents a separate embodiment of the present invention.

The epilepsy of methods and compositions of the present invention is, in another embodiment, an idiopathic epilepsy. In another embodiment, the epilepsy responds to corticosteroids, IgG-depleting therapy, including plasma exchange or plasmapheresis and intravenous immunoglobulin (IVIG). In another embodiment, the epilepsy is associated with partial seizures. In another embodiment, the epilepsy is associated with simple partial seizures. In another embodiment, the epilepsy is associated with complex partial seizures. In another embodiment, the epilepsy is associated with generalized seizures. In another embodiment, the epilepsy is associated with absence (petit mal) seizures. In another embodiment, the epilepsy is associated with myoclonic seizures. In another embodiment, the epilepsy is associated with tonic-clonic (grand mal) seizures.

In another embodiment, the epilepsy is associated with West syndrome. In another embodiment, the epilepsy is associated with Lennox-Gastaut syndrome. In another embodiment, the epilepsy is associated with any other syndrome known in the art.

In another embodiment the epilepsy is of no known cause. In another embodiment the epilepsy is any other type of epilepsy known in the art. Each type of epilepsy represents a separate embodiment of the present invention.

"Cause of" an autoimmune encephalitis, epilepsy, etc, refers, in another embodiment, to a primary cause of the disorder. In another embodiment, the term refers to a contributing cause of the disorder. In another embodiment, the term refers to an indirect causation. In another embodiment, the term refers to causation via an immune response induced by the tumor. In another embodiment, the term refers to a significant cause of the disorder. Each possibility represents a separate embodiment of the present invention.

In another embodiment, the present invention provides a method for diagnosing a tumor in a subject having an encephalitis, comprising the step of testing a body fluid of said subject for an antibody to LGI1, thereby diagnosing a tumor in said subject having said encephalitis. In another embodiment, the presence of the antibody indicates a presence of a tumor in the subject. Each possibility represents a separate embodiment of the present invention.

In another embodiment, the present invention provides a method for detecting a tumor in a subject having an encephalitis, comprising the step of testing a body fluid of said subject for an antibody to LGI1, thereby detecting said tumor in said subject having said encephalitis. In another embodiment, the presence of the antibody indicates the presence of a tumor in the subject. Each possibility represents a separate embodiment of the present invention.

In one embodiment, the present invention provides a method for diagnosing a tumor in a subject having an epilepsy, comprising the step of testing a body fluid of said subject for an antibody to LGI1, thereby diagnosing said tumor in said subject having said epilepsy. In another embodiment, the presence of the antibody indicates the presence of a tumor in the subject. Each possibility represents a separate embodiment of the present invention.

In one embodiment, the present invention provides a method for detecting a tumor in a subject having an epilepsy, comprising the step of testing a body fluid of said subject for an antibody to LGI1, thereby detecting said tumor in said subject having said epilepsy. In another embodiment, the presence of said antibody indicates a presence of a tumor in the subject. Each possibility represents a separate embodiment of the present invention.

In one embodiment, the present invention provides a method of diagnosing or detecting a LGI1-mediated disease in a subject, comprising the step of testing a body fluid of the subject for an antibody to an antibody to LGI1, thereby diagnosing or detecting said LGI1-mediated disease in said subject.

Inventors of the instant application surprisingly and unexpectedly found that LGI1 is the autoantigen of the limbic encephalitis previously attributed to Voltage-gated potassium channels (VGKC). Immunoprecipitation and mass spectrometry showed that patients' antibodies recognize LGI1, a neuronal secreted protein that interacts with pre-synaptic ADAM23 and post-synaptic ADAM22, bridging the synapse. Specific immunostaining of HEK293 cells transfected with LGI1 showed that all patients' serum or CSF, but not controls, recognized LGI1. Co-transfection with LGI1 and its ligands, ADAM22 or ADAM23, changed the pattern of reactivity improving antibody detection.

In another embodiment, the present invention provides a method of diagnosing or detecting a ADAM22 or ADAM23-mediated disease in a subject, comprising the step of testing a body fluid of the subject for an antibody to an antibody to LGI1, thereby diagnosing or detecting said ADAM22 or ADAM23-mediated disease in said subject.

In one embodiment, the invention provides a method of treating autoimmune encephalitis in a subject. In one embodiment, the method comprises the steps of: detecting a tumor associated with an autoimmune encephalitis by testing a body fluid from said subject for an antibody to LGI1, whereby a presence of said antibody indicates the presence of said tumor in said subject and that said tumor is a cause of said autoimmune encephalitis. In another embodiment, the method comprises the step of treating said tumor. In another embodiment, the tumor is treated during the early stage.

In one embodiment, the step of treating said tumor comprises removing said tumor. In another embodiment, the step of treating said tumor comprises radiation therapy. In another embodiment, the step of treating said tumor comprises removing said tumor in combination with radiation therapy. In another embodiment, the step of treating said tumor comprises chemotherapy. In another embodiment, the step of treating said tumor comprises removing said tumor in combination with chemotherapy and radiation therapy In one embodiment, LGI1 protein has the sequence as set forth below:

```
                                                      SEQ ID NO: 2)
MESERSKRMG NACIPLKRIA YFLCLLSALL LTEGKKPAKP KCPAVCTCTK DNALCENARS    60
IPRTVPPDVI SLSFVRSGFT EISEGSFLFT PSLQLLLFTS NSFDVISDDA FIGLPHLEYL   120
FIENNNIKSI SRHTFRGLKS LIHLSLANNN LQTLPKDIFK GLDSLTNVDL RGNSFNCDCK   180
LKWLVEWLGH TNATVEDIYC EGPPEYKKRK INSLSSKDFD CIITEFAKSQ DLPYQSLSID   240
TFSYLNDEYV VIAQPFTGKC IFLEWDHVEK TFRNYDNITG TSTVVCKPIV IETQLYVIVA   300
QLFGGSHIYK RDSFANKFIK IQDIEILKIR KPNDIETFKI ENNWYFVVAD SSKAGFTTIY   360
KWNGNGFYSH QSLHAWYRDT DVEYLEIVRT PQTLRTPHLI LSSSSQRPVI YQWNKATQLF   420
TNQTDIPNME DVYAVKHFSV KGDVYICLTR FIGDSKVMKW GGSSFQDIQR MPSRGSMVFQ   480
PLQINNYQYA ILGSDYSFTQ VYNWDAEKAK FVKFQELNVQ APRSFTHVSI NKRNFLFASS   540
FKGNTQIYKH VIVDLSA                                                 557
```

In another embodiment, the amino acid sequence of LGI1 is a homologue of SEQ ID NO: 2. In another embodiment, the amino acid sequence of LGI1 is a variant of SEQ ID NO: 2. In another embodiment, the amino acid sequence of LGI1 is an isomer of SEQ ID NO: 2. In another embodiment, the amino acid sequence of LGI1 is a fragment of SEQ ID NO: 2. Each possibility represents a separate embodiment of the present invention.

In another embodiment, LGI1 is encoded by a nucleotide sequence having the sequence:

```
                                                           SEQ ID NO: 1)
          gaaagcagaa agctgtttat tttctgtgac atcacttcac tttgccttcg aaggctggtc     60
          tgtgctcagt gttttcgtgg tgatgcaagt cggctctctc ctccagcagt tggatccctc    120
          ccatctcaca gtacctcaca ggtctcttcc cccgagcagt gcattgctgg agcgaggaga    180
          agctcacgaa tcagctgcag gtctctgttt tgaaaaagca gagatacaga ggcagaggaa    240
          aagggtggac tcctatgtga cctgttctta gagcaagaca atcaccatct gaattccaga    300
          agccctgttc atggttgggg atattttctc gactgcatgg aatcagaaag aagcaaaagg    360
          atgggaaatg cctgcattcc cctgaaaaga attgcttatt tcctatgtct cttatctgcg    420
          cttttgctga ctgagggaa gaaaccagcg aagccaaaat gccctgccgt gtgtacttgt    480
          accaaagata atgctttatg tgagaatgcc agatccattc cacgcaccgt tcctcctgat    540
          gttatctcat tatcctttgt gagatctggt tttactgaaa tctcagaagg gagttttta    600
          ttcacgccat cgctgcagct cttgttattc acatcgaact cctttgatgt gatcagtgat    660
          gatgctttta ttggtcttcc acatctagag tatttattca tagaaaacaa caacatcaag    720
          tcaatttcaa gacatacttt ccggggacta agtcattaa ttcacttgag ccttgcaaac    780
          aacaatctcc agacactccc aaaagatatt ttcaaaggcc tggattcttt aacaaatgtg    840
          gacctgaggg gtaattcatt taattgtgac tgtaaactga atggctagt ggaatggctt    900
          ggccacacca atgcaactgt tgaagacatc tactgcgaag gcccccaga atacaagaag    960
          cgcaaaatca atagtctctc ctcgaaggat ttcgattgca tcattacaga atttgcaaag   1020
          tctcaagacc tgccttatca atcattgtcc atagacactt tttcttattt gaatgatgag   1080
          tatgtagtca tcgctcagcc ttttactgga aaatgcattt tccttgaatg ggaccatgtg   1140
          gaaaagacct tccggaatta tgacaacatt acaggcacat ccactgtagt atgcaagcct   1200
          atagtcattg aaactcagct ctatgttatt gtggcccagc tgtttggtgg ctctcacatc   1260
          tataagcgag acagttttgc aaataaattc ataaaaatcc aggatattga aattctcaaa   1320
          atccgaaaac ccaatgacat tgaaacattc aagattgaaa acaactggta ctttgttgtt   1380
```

```
                                    -continued
gctgacagtt caaaagctgg tttactacc atttacaaat ggaacggaaa cggattctac   1440 tccatcaat  ccttacacgc gtggtacagg gacactgatg tggaatatct agaaatagtc   1500
agaacacctc agacactcag aacgcctcat ttaattctgt ctagtagttc ccagcgtcct   1560
gtaatttatc agtggaacaa agcaacacaa ttattcacta accaaactga cattcctaac   1620
atggaggatg tgtacgcagt gaagcacttc tcagtgaaag gggacgtgta catttgcttg   1680
acaagattca ttggtgattc caaagtcatg aaatggggag gctcctcgtt ccaggatatt   1740
cagaggatgc catcgcgagg atccatggtg ttccagcctc ttcaaataaa taattaccaa   1800
tatgcaattc ttggaagtga ttactccttt actcaagtgt ataactggga tgcagagaaa   1860
gccaaatttg tgaaatttca ggaattaaat gttcaggcac caagatcatt cacacatgtg   1920
tccattaata agcgtaattt tcttttttgct tccagtttta agggaaatac acagatttac   1980
aaacatgtca tagttgactt aagcgcatga gacaccaaat tctgtggctg ccatcagaaa   2040
ttttctacag tacatgaccc ggatgaactc aatgcatgat gactcttctt atcacacttg   2100
caaatgaatg cctttcaaac attgagactg ctagaaccaa gcactaccag tatctccatc   2160
cttaactgtc cagtccagtg atgtgggaag ttaccttta taagacaaaa tttaattgtg   2220
taactgttct ttgcagtgaa gatgtgtaaa taagcgttta atggtatctg ttactccaaa   2280
aagaaatatt aatatgtact tttccattta tttattcatg tgtacagaaa caactgccaa   2340 ataaatgtt  tacattttct ttcata                                       2366
```

In another embodiment, the nucleic acid sequence of LGI1 is a homologue of SEQ ID NO: 1. In another embodiment, the nucleic acid sequence of LGI1 is a variant of SEQ ID NO: 1. In another embodiment, the nucleic acid sequence of LGI1 is an isomer of SEQ ID NO: 1. In another embodiment, the nucleic acid sequence of LGI1 is a fragment of SEQ ID NO: 1. Each possibility represents a separate embodiment of the present invention.

The epitope recognized by an antibody detected by a method of the present invention is, in another embodiment, a conformational epitope. In another embodiment, the epitope is a linear epitope. In another embodiment, the epitope is any other type of epitope known in the art. Each possibility represents a separate embodiment of the present invention.

In one embodiment, ectopic expression of LGI1 by nervous tissue contained in the tumors contributes to break immune tolerance. In another embodiment, a combination of factors such as an adjuvant effect of the prodromal viral-like illness that occur in most subjects, and a genetic predisposition in certain embodiments, play additional roles in the initiation of the immune response tested for using the diagnosis methods described herein.

In one embodiment, a pathogenic role of antibodies in paraneoplastic anti-LGI1 encephalitis is shown by the correlation between patients' symptoms and antibody titers.

In another embodiment, the subject exhibits antibodies that react with an extracellular neuronal antigen. In another embodiment, the subject exhibits antibodies that react with an antigen exposed on the cell surface of a neuron. In another embodiment, patients with antibodies to extracellular antigens exhibit, under the conditions utilized herein, enhanced responsiveness to immune therapy.

In some embodiments, antibodies of the invention bind specifically to an epitope in LGI1. In one embodiment, antibodies of the invention bind specifically to Epilepsy Associated Repeat (EAR) domain. In another embodiment, antibodies of the invention neutralize the interaction between LGI1 and its interacting protein, for example, ADAM22 and ADAM23. In another embodiment, antibodies of the invention inhibit the binding of LGI1 to its binding protein, for example, ADAM22 and ADAM23.

In another embodiment, a method of the present invention utilizes, detects, or tests for a target antigen identified by a method disclosed herein. In another embodiment, the target antigen is identified by a library screening technique. In another embodiment, the target antigen is identified by cDNA library screening. In another embodiment, the target antigen is identified by reactivity with cultured neurons. In another embodiment, the target antigen is identified by immunoprecipitation by patient's antibodies. Each possibility represents a separate embodiment of the present invention.

Methods for testing a reactivity of a body fluid against neuronal antigens are well known in the art. In one embodiment, enzyme-linked immunoabsorption assay (ELISA) is used to test for the presence of an antibody. In another embodiment, immunocytochemistry is used to test for the presence of an antibody. In another embodiment, immunoprecipitation is used to test for the presence of an antibody. In another embodiment, one of the methods enumerated herein is utilized. In another embodiment, neuronal tissue is fixed with PFA. In another embodiment, any other method known in the art is utilized. Each possibility represents a separate embodiment of the present invention.

In another embodiment, the present invention provides a kit comprising a compound or composition utilized in performing a method of the present invention. In another embodiment, the present invention provides a kit comprising a composition, tool, or instrument of the present invention. Each possibility represents a separate embodiment of the present invention.

Methods and kits for detection of antibodies are well known in the art, and are described, for example, in Ances B M et al (Treatment-responsive limbic encephalitis identified by neuropil antibodies: MRI and PET correlates. Brain 2005; 128:1764-1777) and Vitaliani et al (Paraneoplastic encephalitis, psychiatric symptoms, and hypoventilation in ovarian teratoma. Ann Neurol 2005; 58:594-604). Each possibility represents a separate embodiment of the present invention.

Methods for diagnosing limbic encephalitis (LE) are well known in the art. In another embodiment, patients with LE develop subacute confusion, irritability, depression, sleep disturbances, seizures, short-term memory loss, and/or dementia. In another embodiment, the pathological substrate of LE is an inflammatory disorder that predominantly involves the limbic system (hippocampi, amygdala, and cingulate gyrus). In another embodiment, biopsy and autopsy studies demonstrate interstitial and perivascular infiltrates of T cells, and less frequently B cells, along with microglial activation, neuronal degeneration, and/or gliosis. In another embodiment, inflammatory infiltrates are found in areas distant from the limbic system. In another embodiment, the infiltrates remain mild and clinically silent. In another embodiment, the infiltrates become prominent and develop into a disorder called encephalomyelitis. Additional methods of diagnosing LE are described, for example, in Gultekin S H et al (Paraneoplastic limbic encephalitis: neurological symptoms, immunological findings and tumour association in 50 patients. Brain 2000; 123:1481-1494). Each possibility represents a separate embodiment of the present invention.

In another embodiment, an antigen of the present invention is homologous to a peptide disclosed herein. The terms "homology," "homologous," etc, when in reference to any protein or peptide, refer, in one embodiment, to a percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

Homology is, in another embodiment, determined by computer algorithm for sequence alignment, by methods well described in the art. For example, computer algorithm analysis of nucleic acid sequence homology can include the utilization of any number of software packages available, such as, for example, the BLAST, DOMAIN, BEAUTY (BLAST Enhanced Alignment Utility), GENPEPT and TREMBL packages.

In another embodiment, "homology" refers to identity to a sequence selected from SEQ ID NO: 1-2 of greater than 70%. In another embodiment, "homology" refers to identity to a sequence selected from SEQ ID NO: 1-2 of greater than 72%. In another embodiment, "homology" refers to identity to one of SEQ ID NO: 1-2 of greater than 75%. In another embodiment, "homology" refers to identity to a sequence selected from SEQ ID NO: 1-2 of greater than 78%. In another embodiment, "homology" refers to identity to one of SEQ ID NO: 1-2 of greater than 80%. In another embodiment, "homology" refers to identity to one of SEQ ID NO: 1-2 of greater than 82%. In another embodiment, "homology" refers to identity to a sequence selected from SEQ ID NO: 1-2 of greater than 83%. In another embodiment, "homology" refers to identity to one of SEQ ID NO: 1-2 of greater than 85%. In another embodiment, "homology" refers to identity to one of SEQ ID NO: 1-2 of greater than 87%. In another embodiment, "homology" refers to identity to a sequence selected from SEQ ID NO: 1-2 of greater than 88%. In another embodiment, "homology" refers to identity to one of SEQ ID NO: 1-2 of greater than 90%. In another embodiment, "homology" refers to identity to one of SEQ ID NO: 1-2 of greater than 92%. In another embodiment, "homology" refers to identity to a sequence selected from SEQ ID NO: 1-2 of greater than 93%. In another embodiment, "homology" refers to identity to one of SEQ ID NO: 1-2 of greater than 95%. In another embodiment, "homology" refers to identity to a sequence selected from SEQ ID NO: 1-2 of greater than 96%. In another embodiment, "homology" refers to identity to one of SEQ ID NO: 1-2 of greater than 97%. In another embodiment, "homology" refers to identity to one of SEQ ID NO: 1-2 of greater than 98%. In another embodiment, "homology" refers to identity to one of SEQ ID NO: 1-2 of greater than 99%. In another embodiment, "homology" refers to identity to one of SEQ ID NO: 1-2 of 100%. Each possibility represents a separate embodiment of the present invention.

In another embodiment, homology is determined via determination of candidate sequence hybridization, methods of which are well described in the art (See, for example, "Nucleic Acid Hybridization" Hames, B. D., and Higgins S. J., Eds. (1985); Sambrook et al., 2001, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y). In other embodiments, methods of hybridization are carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA.

Protein and/or peptide homology for any AA sequence listed herein is determined, in another embodiment, by methods well described in the art, including immunoblot analysis, or via computer algorithm analysis of AA sequences, utilizing any of a number of software packages available, via established methods. Some of these packages include the FASTA, BLAST, MPsrch or Scanps packages, and, in another embodiment, employ the use of the Smith and Waterman algorithms, and/or global/local or BLOCKS alignments for analysis, for example. Each method of determining homology represents a separate embodiment of the present invention.

In another embodiment of the present invention, "nucleic acids" or "nucleotide" refers to a string of at least two base-sugar-phosphate combinations. The term includes, in one embodiment, DNA and RNA. "Nucleotides" refers, in one embodiment, to the monomeric units of nucleic acid polymers. RNA is, in one embodiment, in the form of a tRNA (transfer RNA), snRNA (small nuclear RNA), rRNA (ribosomal RNA), mRNA (messenger RNA), anti-sense RNA, small inhibitory RNA (siRNA), micro RNA (miRNA) and ribozymes. The use of siRNA and miRNA has been described (Caudy A A et al, Genes & Devel 16: 2491-96 and references cited therein). DNA can be, in other embodiments, in form of plasmid DNA, viral DNA, linear DNA, or chromosomal DNA or derivatives of these groups. In addition, these forms of DNA and RNA can be single, double, triple, or quadruple stranded. The term also includes, in another embodiment, artificial nucleic acids that contain other types of backbones but the same bases. In one embodiment, the artificial nucleic acid is a PNA (peptide nucleic acid). PNA contain peptide backbones and nucleotide bases and are able to bind, in one embodiment, to both DNA and RNA molecules. In another embodiment, the nucleotide is oxetane modified. In another embodiment, the nucleotide is modified by replacement of one or more phosphodiester bonds with a phosphorothioate bond. In another embodiment, the artificial nucleic acid contains any other variant of the phosphate backbone of native nucleic acids known in the art. The use of phosphothiorate nucleic acids and PNA are known to those skilled in the art, and are described in, for example, Neilsen P E, Curr Opin Struct Biol 9:353-57; and Raz N K et al Biochem Biophys Res Commun. 297:1075-84. The production and use of nucleic acids is known to those skilled in art and is described, for example, in Molecular Cloning, (2001), Sambrook and Russell, eds. and Methods in Enzymology: Methods for molecular cloning in eukaryotic cells (2003) Purchio and G. C. Fareed. Each nucleic acid derivative represents a separate embodiment of the present invention.

All literature references cited in the present specification are hereby incorporated by reference in their entirety.

The following examples are presented in order to more fully illustrate the preferred embodiments of the invention. They should in no way be construed, however, as limiting the broad scope of the invention.

EXAMPLES

Materials and Methods

Patients and Controls

Serum or CSF samples were obtained from 57 patients with limbic encephalitis and antibodies to VGKC-related proteins and 148 control individuals including patients with the following disorders: 41 with acute encephalopathies suspected to be autoimmune (5 with clinical and MRI features of classic limbic encephalitis), 27 anti-NMDAR encephalitis, 17 viral encephalitis, 10 limbic encephalitis and AMPA receptor antibodies, 8 Rasmussen's encephalitis, 38 acquired neuromyotonias (all confirmed electrophysiologically; 3 with positive $^{125}$I-α-dendrotoxin RIA and 35 negative), 2 Morvan's syndrome, and 5 subacute neuropathies. Clinical information was obtained from the authors and treating physicians. Studies were approved by the University of Pennsylvania Institutional Review Board.

Serum or CSF were considered positive for VGKC antibodies when they fulfilled the following criteria, 1) showed a previously defined pattern of immunostaining with the neuropil of adult rat brain, 2) reacted with the cell surface of non-permeabilized rat hippocampal neurons, and/or 3) had antibodies identified by $^{125}$I-α-dendrotoxin RIA in several commercial laboratories.

Immunohistochemistry on Rat Brain and Neuronal Cultures

Female Wistar rats were euthanized and the brain was removed, sagittally sectioned, immersed in 4% paraformaldehyde at 4° C. for 1 hour, cryoprotected with 40% sucrose for 24 hours, and snap frozen in chilled isopentane. Immunohistochemistry methods using a standard avidin-biotin peroxidase method were applied using patients serum (diluted 1:200) or CSF (1:5), followed by the appropriate secondary antibodies, as reported. Similar studies were carried out using patients' serum and CSF after immunoabsorption with LGI1.

Rat hippocampal neuronal cultures were prepared as reported. Fourteen days in vitro (div) live neurons grown on coverslips were exposed for 1 hour at 37° C. to the patients' or control serum (final dilution 1:200) or CSF (1:10). After removing the media and extensive washing with phosphate-buffered saline (PBS), neurons were incubated with anti-human IgG Alexa Fluor secondary antibody diluted 1:1000 (Molecular Probes, Oreg.). Results were photographed under a fluorescent microscope using a Zeiss Axioskop (Zeiss, Thornwood, N.Y.).

Immunoprecipitation, Mass Spectrometry, and Immunoblot

Live neurons obtained as above, were grown in 100 mm wells (density $10^6$ neurons/well), and incubated at 37° C. with filtered patient serum (diluted 1:500) for 1 hour. Neurons were then washed with PBS, lysed with buffer (NaCl 150 mM, EDTA 1 mM, tris(hydroxymethyl)aminomethane [Tris]-HCl 100 mM, deoxycholate acid 0.5%, 1% Triton X-100 [Sigma Labs, St. Louis, Mo.], pH 7.5) containing protease inhibitors (P8340; Sigma Labs), and centrifuged at 16.1×10$^3$ g for 20 minutes at 4° C. The supernatant was retained and incubated with protein A/G agarose beads (20423; Pierce, Rockford, Ill.) overnight at 4° C., centrifuged, and the pellet containing the beads with patients' antibodies bound to the target cell surface antigen was then washed with PBS, aliquoted, and kept at −80° C. An aliquot of this pellet was resuspended in Laemmli buffer, boiled for 10 minutes, separated in a 4 to 15% sodium dodecyl sulfate polyacrylamide gel electrophoresis, and the proteins visualized with EZBlue gel staining (G1041; Sigma Labs). Distinctive protein bands precipitated by patient serum were excised from the gel and analyzed using mass spectrometry at the proteomic facility at the University of Pennsylvania. After characterization of the antigen, frozen aliquots of the indicated pellets were separated in a sodium dodecyl sulfate polyacrylamide gel electrophoresis, transferred to nitrocellulose (162-0115; Bio-Rad, Hercules, Calif.), and probed with the indicated LGI1 antibody (made in rabbit, dilution 1:500; Ab30868, Abcam, Cambridge, Mass.). The reactivity was developed using the appropriate biotinylated secondary antibodies (1:2000) and the avidin-biotin peroxidase, diaminobenzidine method.

Protein bands from the gels were cut and sent for mass spectrometry to the Proteomics Core Facility of the Genomics Institute at the Abramson Cancer Center (University of Pennsylvania). Protein bands were trypsin digested and analyzed with a nano liquid chromatography (nano LC)/nanospray/linear ion trap (LTQ) mass spectrometer (Thermo Electron Corporation, San Jose, Calif.) as reported. Briefly, 3 1 trypsin digested sample was injected with autosampler from Eksigent (Dublin, Calif.). The digested samples were separated on a 10 cm C18 column, using nano LC from Eksigent with 200 l/minute flow rate, 45 minute gradient. Online nanospray was used to spray the separated peptides into LTQ, and Xcalibur software (Thermo Scientific, Waltham, Mass.) was utilized to acquire the raw data. The raw data files were searched using Mascot (Matrix Science, Boston, Mass.) against the NCBI and Swissprot databases (Swiss Institute of Bioinformatics (Basel, Switzerland). The cutoff for confident protein identification was ≥70.

Immunocytochemistry on HEK293 Cells

HEK293 cells were transfected using lipofectamine 2000 (Invitrogen 11668027) with plasmid containing LGI1 (sc116925, Origene, Rockville, Md.), ADAM22 or ADAM23 (both constructs containing an HA tag; kindly provided by Drs. Yuko Fukata and Masaki Fukata, National Institute for Physiological Sciences, National Institutes of Natural Sciences, Okazaki, Japan), or co-transfected with LGI1+ ADAM22 or LGI1+ADAM 23. In other experiments, HEK293 cells were transfected with Kv1.1 and Kv1.4 (kindly provided by Cr. Steven Scherer, University of Pennsylvania). Given that LGI1 is a secreted protein we aimed at increasing intracellular antigen content. Therefore, in experiments using single LGI1 transfections, 100 ng/ml Brefeldin A (#9972, Cell signaling technology, Boston, Mass., USA) was added to the media two hours before incubation with patients' samples. This fungal metabolite inhibits transport from the endoplasmic reticulum to the Golgi apparatus and is able to prevent protein secretion. Cells transfected with plasmids without insert and non-transfected served as controls. Cells were grown for 24 hours after transfection, fixed with 4% paraformaldehyde, permeabilized with 0.2% Triton X-100 (Sigma), and incubated for 1 hour at 37° C. with patients' or control serum (final dilution 1:200) or CSF (1:10) and commercial antibodies to LGI1 (made in rabbit, dilution 1:1000; Ab30868, Abcam, Cambridge, Mass.), HA-tag (made in chicken, dilution 1:100; 70-CH-18, Fitzgerald industries, Acton, Mass.), Kv1.1 (made in mouse, dilution 1:50; Clone 20/78, NeuroMab, Davis, Calif.), or Kv1.4 (made in rabbit, dilution 1:50, Alomone labs, Jerusalem, Israel). Double immunolabeling was performed using the appropriate Alexa-Fluor secondary antibodies diluted 1:1000 (Molecular Probes, Oreg.).

In another set of experiments, HEK293 cells transfected with ADAM22 or ADAM23 were washed and the media was replaced for 1 hour at 37° C. with LGI1-enriched media separated from HEK293 cells expressing LGI1. Subsequently, cells were washed, fixed, permeabilized with 0.2% Triton X-100, and incubated with patients' or control serum or CSF at dilutions as above, and a chicken antibody against HA-tag (as above), for 1 hour at 37° C. After washing, the reactivity of patients' antibodies with LGI1 bound to ADAM22 or ADAM23 was determined by double immunolabeling with the appropriate Alex-Fluor secondary antibodies against human and chicken IgG.

HEK293 cells transfected with CASPR2 (human sequence, a gift of Dr. Elior Peles, The Weizmann Institute of Science, Israel) were tested as above with patients' or control serum (1:200) or CSF (1:10) and a commercial antibody to CASPR2 (made in rabbit; Abcam, dilution 1:1000; Ab33994, Cambridge, Mass.).

Immunoabsorption with LGI1

Serum diluted 1:200 was serially incubated with 6 wells containing fixed, permeabilized HEK293 cells expressing LGI1 or cells transfected with plasmid without insert. After five sequential passes of 1 hour each, the serum was applied to sections of rat brain and the reactivity developed using the above indicated avidin-biotin-peroxidase method.

Immunohistochemistry with Wild Type and Lgi1-Null Mice

Wild-type and Lgi1-null mice were generated and genotyped as previously reported (Yu et al., 2010). The brains were removed, sagittally sectioned, fixed for 1 hour in 4% PFA, cryoprotected with 40% sucrose for 24 hours, and snap frozen in chilled isopentane. Immunohistochemistry using a standard avidin-biotin peroxidase method was applied using patients' serum (diluted 1:200) or CSF (1:5), followed by the secondary antibodies, as reported.

Example 1

Immunoprecipitation of LGI1 with Sera of Patients with Limbic Encephalitis

Figures 1, 1A, 1B:
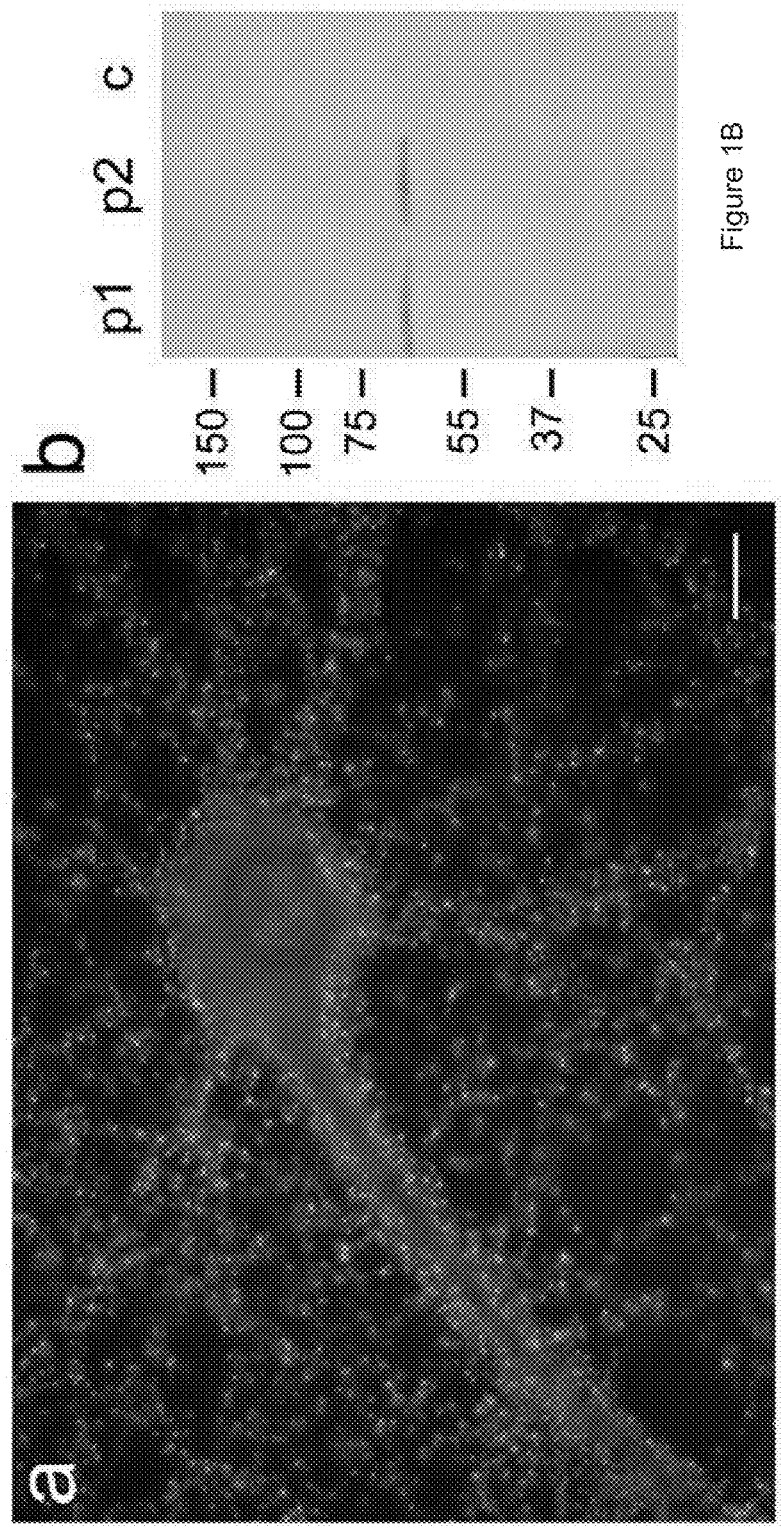
FIG. 1: Immunoprecipitation of LGI1 by serum of patients with limbic encephalitis and antibodies attributed to VGKC. Antibodies of patients with antibodies attribute to VGKC react with the cell surface of cultured live, not permeabilized, rat hippocampal neurons (A); scale bar=10 μm. (B) Immunoprecipitation of the target antigen and mass spectrometry demonstrated that the antigen was LGI1. Immunoblot of rat neuronal cell surface immunoprecipitates by two patients' sera (p1, p2) shows that these precipitates specifically react with a commercial antibody against LGI1. Lane c corresponds to the precipitate using a control serum.

To determine the target autoantigen, sera of two patients with limbic encephalitis and antibodies previously attributed to VGKC were used in experiments of immunoprecipitation. Both sera had antibodies confirmed with all three criteria indicated above (FIG. 1a shows the neuronal cell surface binding). LGI1 was identified as the target antigen by immunoprecipitation using patients' serum samples and peptide sequence recognition by mass spectrometry. This resulted in a score of 261 for the following peptide sequences: K.AGFTTIYK.W (SEQ ID NO: 3), K.IQDIEVLK.I (SEQ ID NO: 4), K.FQELNVQAPR.S (SEQ ID NO: 5), K.GLDSLTNVDLR.G (SEQ ID NO: 6), and K.WGGSSFQDIQR.M (SEQ ID NO: 7). Results were confirmed by immunoblotting the immunoprecipitates with an antibody specific for LGI1.

Example 2

Figures 2A, 2B:
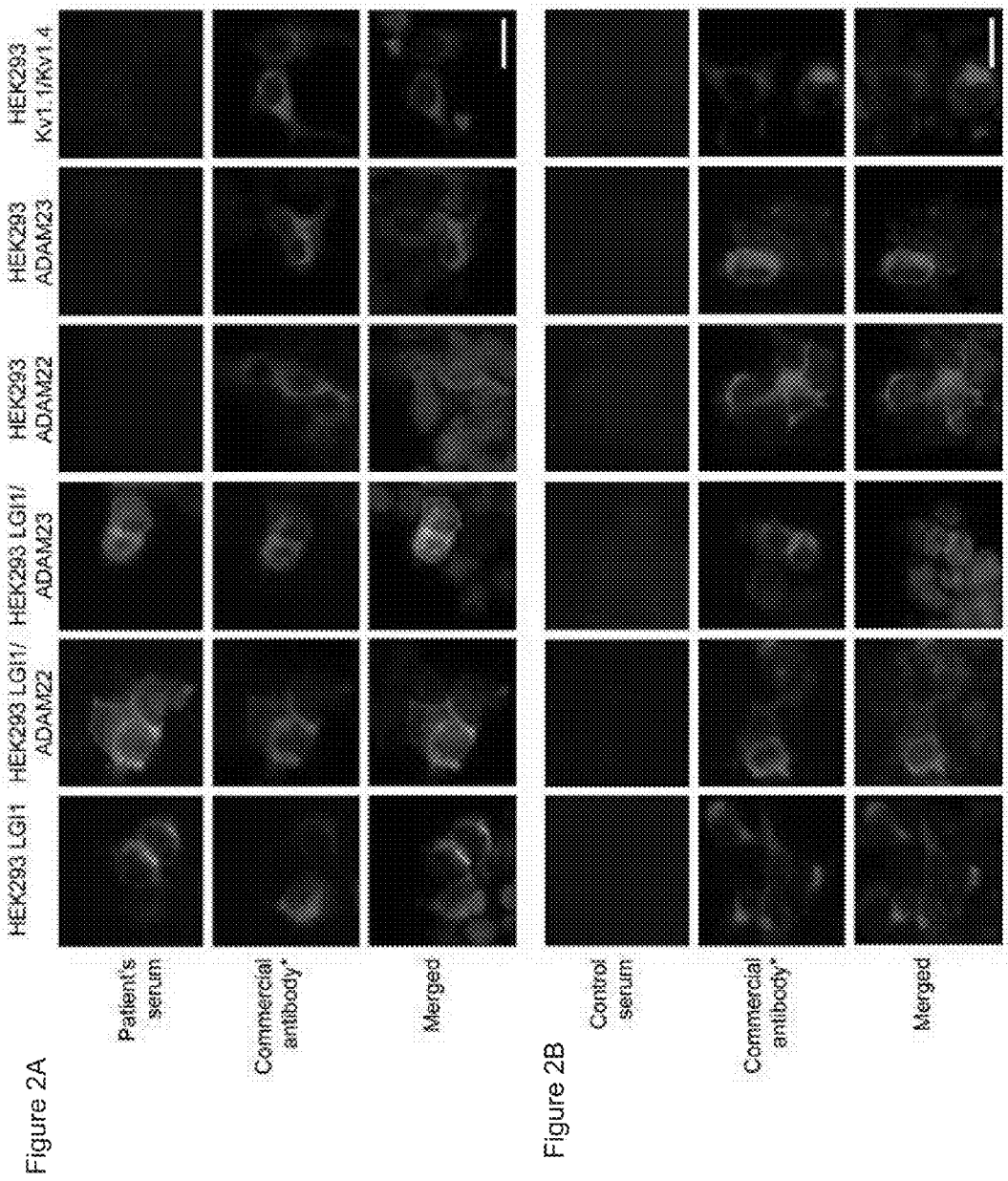

LGI1 is the Antigen of Limbic Encephalitis and Antibodies Previously Attributed to VGKC To determine if LGI1 was recognized by all patients' antibodies, HEK293 cells were transfected with LGI1, permeabilized, and immunostained with patients' serum and CSF. These studies demonstrated that all 57 patients with limbic encephalitis and antibodies attributed to VGKC had serum and CSF antibodies against LGI1. Patients' antibody reactivity was often clustered in the cytoplasm, without uniform distribution on the cell surface, and showed imperfect co-localization with the reactivity of a monoclonal antibody against LGI1 (FIG. 2a, column "HEK293 LGI1"). Given that LGI1 is a secreted protein, we reasoned that blocking the secretion of the protein with Brefeldin A would increase the pattern of reactivity. Indeed, experiments in which LGI1 transfected cells were treated for 2 hours with Brefeldin A showed a substantial increase of reactivity with patients' samples. Additionally, since LGI1 normally interacts with the synaptic proteins ADAM22 and ADAM23, we determined whether patients' antibody reactivity improved after co-expressing LGI1 with ADAM22 or ADAM23. These experiments enhanced the localization of LGI1 to the cell membrane and also improved the reactivity with patients' antibodies. Moreover, the reactivity with LGI1 co-localized with the expression of ADAM22 or ADAM23 suggesting a close interaction between LGI1 and these two proteins (FIG. 2a, columns "HEK293 LGI1/ADAM22", and "HEK293 LGI1/ADAM23"). In contrast, patient's antibodies did not bind single expressed ADAM22 or ADAM23 (FIG. 2a, columns "HEK293 ADAM22" and "HEK293 ADAM23"). Furthermore, the reactivity of patients' antibodies with Kv1.1 was assessed by co-transfection of this subunit with Kv1.4 as this has been reported to increase cell surface expression of the Kv1.1. No reactivity was found with Kv1.1 or Kv1.4 subunits (FIG. 2a, column "HEK293 Kv1/1/Kv1.4") even though the tested samples had VGKC antibodies based on the $^{125}$I-α-dendrotoxin RIA. None of the 148 control patients had antibodies against LGI1 (FIG. 2b). These studies show that LGI1 is the target autoantigen of antibodies from patients with limbic encephalitis previously attributed to VGKC, and that the reactivity of the antibodies is easier to determine when LGI1 is co-expressed with one of its synaptic receptors, ADAM22 or ADAM23.

We next examined whether patients' antibodies recognize the secreted form of LGI1. For these experiments live cells transfected with ADAM22 or ADAM23 were treated with media enriched with LGI1. This media was isolated from HEK293 cells transfected with LGI1. After applying the LGI1-containing media to live cells expressing ADAM22 or ADAM23, the patients' samples, but not controls, showed distinctive reactivity that co-localized with the cell surface of HEK293 cells specifically expressing ADAM22 or ADAM23 (FIG. 3). Because patients' antibodies do not react with ADAM22 or ADAM23 expressed in isolation (see above), these findings indicate that the antibodies specifically recognize secreted LGI1 bound on the cell surface to ADAM22 or ADAM23.

Example 3

LGI1 Immunoabsorption and Lgi1-Null Mice Abrogate Patients' Antibody Reactivity

To confirm that LGI1 is the main target antigen, patient's serum samples were immunoabsorbed with cells transfected with LGI1 or plasmid control, and the reactivity of the serum determined using rat brain immunohistochemistry. This study showed that immunoabsorption with LGI1 abrogated the reactivity of patient's serum with rat brain (FIG. 4).

Figure 6:
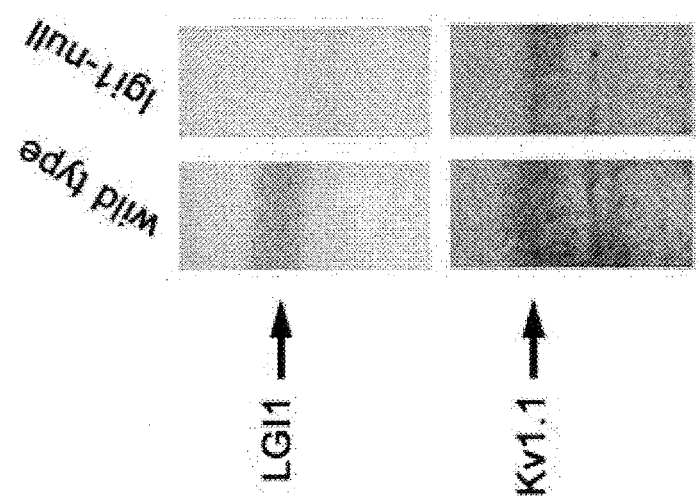

To further confirm that LGI1 is the autoantigen of this disorder comparative brain immunohistochemistry with wild-type and Lgi1-null mice was used. These mutant mice were obtained using a mouse chromosome engineering strategy to create a null mutation for the gene ortholog encoding LGI1. The Lgi1-null mutant mice show no gross overall developmental abnormalities from routine histopathological analysis; these mice and similar models of genetic deletion of LGI1 show brain eression of Kv1 subunits of VGKC (FIG. 6). Brain sections of wild type and Lgi1-null mice were immunostained with samples of 14 patients (7 sera and 7 CSF) randomly selected by use of an online random integer generator (www.random.org/integers/) from 35 patients tested positive by $^{125}$I-α-dendrotoxin RIA. These studies showed that patients' antibodies produced the characteristic pattern of neuropil immunostaining in the wild-type mice, whereas all reactivity was abrogated in the Lgi1-null mice (FIG. 5). These findings define LGI1 as the main autoantigen of limbic encephalitis previously attributed to VGKC antibodies.

Example 4

Clinical Features of Patients with LGI1 Antibodies

Demographic information, clinical features, treatment and outcome of patients with LGI1 antibodies are summarized in Table 1.

TABLE 1

Clinical Features of 57 patients with LGI1 antibodies

| Clinical Features | Patients |
|---|---|
| Males | 65% |
| Age | Median 60; range 30-80 |
| Tumor (information for 53) | 11% with tumor * |
| Clinical diagnosis of limbic encephalitis | 100% |
| Memory loss | 100% |
| Myoclonus (45 with detailed neurological exam) | 40% |
| Hyponatremia (information for 47) | 60% |
| Median serum sodium, range | 128 mM, 118-132 mM. |
| Seizures (information for 51) | 82% † |
| MRI (information for 51) | |
| Increased T2 signal involving medial temporal lobe(s) | 84% |
| EEG (information for 34) | |
| Any abnormality | 73% |
| Seizures | 32% |
| Epileptiform discharges | 12% |
| Diffuse or focal slowing | 32% |
| Lumbar Puncture (information for 46) | |
| Any abnormality | 41% |
| Elevated Protein | 28% |
| Lymphocytic pleocytosis | 17% |
| Treatments (information for 50) | |
| Any treatment | 96% |
| Steroids | 84% |
| IVIG | 62% |
| Plasma exchange | 6% |
| Other treatments | 12% ** |
| Clinical Outcomes (information for 50) | |
| Full recovery | 24% |
| Mild disability | 54% |
| Moderate Disability | 16% |
| Death | 6% |
| Follow-up visits (information for 33) | |
| Median number of months after initial treatment, range | 18 months, range 2-60 |
| Relapse reported | 18% (6 of 33 patients) |
| $^{125}$I-α-dendrotoxin RIA (information for 35) | |
| Tested positive | 100% |
| Median titer, range | 1054, range 105-7600 |

* Tumors: 1 lung, 2 thyroid, 1 renal cell, 1 ovarian teratoma, 1 thymoma.
† Seizure onset was focal in 95% of cases where localization was determined (n = 38); 11% of patients with seizures had convulsive or non-convulsive status epilepticus.
** Other treatments include rituximab (3), azathioprine (2), and cyclosporine (1).

The median age of the patients was 60 years (range 30-80) and 65% were male. All patients had clinical or radiological features of limbic encephalitis; 82% had seizures (frequently involving the temporal lobes), and 84% had typical FLAIR/T2 increased signal involving one or both medial temporal lobes on brain MRI. Detailed examination of 45 patients showed that 18 (40%) had myoclonus. Hyponatremia, defined as serum sodium <135 mM, occurred in 28 of 47 patients (60%), and the CSF was abnormal in 19 of 46 cases (41%). Six of 51 patients (11%) who underwent extensive tumor screening including CT of the chest, abdomen and pelvis or FDG-PET had systemic tumors. All 6 patients with tumors had tumor therapy. Most patients received IVIG, glucocorticoids, and/or plasma exchange and 6 were also treated with other agents. Seventy-eight percent of the patients had good outcomes (24% full recovery, 54% mild residual memory impairment preventing full return to work), 16% residual deficits, and 3 patients died (1 lung cancer; 1 pneumonia/sepsis; 1 unclear cause). Relapses occurred in 18% of patients for whom follow-up information was available.

Example 5

Immunoprecipitation of CASPR2 and Assessment of Antibodies Against CASPR2

Among the 148 patients without LGI1 antibodies, 5 had "VGKC" antibodies as per $^{125}$I-α-dendrotoxin RIA. They included 3 patients with neuromyotonia, 1 with Morvan's syndrome, and 1 with severe encephalitis and seizures. To isolate the autoantigen we used the immunoprecipitation method described above, with serum of the patient with encephalitis and seizures. This resulted in the isolation of several peptide sequences of rat CASPR2 (score 65; R.TNSPLQVK.T (SEQ ID NO: 8); -.MLYSDTGR.N (SEQ ID NO: 9); R.HDLQHAVVAR.Y (SEQ ID NO: 10)). Subsequently, HEK293 cells transfected with a plasmid containing the human sequence of CASPR2 were used in a immunocytochemical assay. This cell based assay confirmed that the patient's serum had antibodies against CASPR2 (FIG. 7a). Among the other 4 patients with "VGKC" antibodies only the case with Morvan's syndrome had CASPR2 antibodies (FIG. 7b). To assess whether CASPR2 was recognized by serum or CSF of patients with limbic encephalitis or neuromyotonia, we examined all 57 patients (30 CSF, 27 sera) with limbic encephalitis and LGI1 antibodies, and the sera of 35 patients with neuromyotonia ("VGKC" antibody negative). Only 1 patient from each group had antibodies against CASPR2

(FIG. 7c). Overall, these studies demonstrate that CASPR2 antibodies occur in 3% of patients with neuromyotonia and 2% of patients with limbic encephalitis.

This study demonstrates that the target antigen of antibodies of patients with limbic encephalitis previously attributed to VGKC is in fact LGI1, a neuronal secreted protein that functions as ligand for two epilepsy-related proteins, ADAM22 and ADAM23.[20,21] Four different sets of experiments establish LGI1 as the autoantigen of this disorder, 1) direct immunoprecipitation of LGI1 with patients' antibodies, 2) specific immunostaining of HEK293 cells expressing LGI1 with serum and CSF from a large series of patients, 3) specific abrogation of patients' serum and CSF brain reactivity after immunoabsorption with LGI1-expressing cells, and 4) comparative brain immunostaining of wild type and Lgi1-null mutant mice, demonstrating lack of reactivity of patients' serum and CSF with LgI1-null mice.

The fact that LGI1 is secreted makes the assessment of the reactivity of patients' serum and CSF more difficult. For example, when HEK293 cells were transfected to express LGI1, the reactivity of patients' antibodies was often weak and irregularly clustered in the cytoplasm of the cells. The reactivity substantially improved after treating the cells with Brefeldin A, and further improvement was noted when LGI1 was co-transfected with ADAM22 or ADAM23, regardless of the use of Brefeldin A. These co-transfections resulted in a uniform distribution of LGI1 in the cytoplasm and membrane of the cells that co-localized with ADAM22 or ADAM23 and was readily recognized by patients' antibodies. Patients' antibodies not only reacted with LGI1 expressed in the cells, but also with extracellulary secreted LGI1 bound to ADAM22 or ADAM23. Moreover, the findings reveal a human disorder that associates with antibodies to intracellular, cell surface, and secreted LGI1, providing an unambiguous diagnostic test for the detection of these antibodies.

Since the focus of this study was the isolation of the autoantigen of limbic encephalitis previously attributed to VGKC, all patients had symptoms or MRI features identified by their physicians as "limbic encephalitis". Clinical seizures, mostly involving the temporal lobes were identified in 82% of the patients, and 40% had myoclonus, a frequent feature noted in mice with deleted LGI1. Hyponatremia, often attributed to the syndrome of inappropriate antidiuretic hormone section (SIADH), occurred in 62% of the patients, and it could be related to the expression of LGI1 in hypothalamus and kidney. Most patients received immunotherapy, and 78% had substantial clinical recovery.

In contrast to previous studies in which antibodies attributed to VGKC were identified in a subgroup of patients with neuromyotonia, we did not find LGI1 antibodies in 38 patients with this disorder, even though 3 of them were "VGKC antibody" positive as determined by $^{125}$I-α-dendrotoxin RIA. Given that α-dendrotoxin binds to Kv1.1, Kv1.2 and Kv1.6 subunits of the VGKC, the commercial "VGKC antibody test" which is based on serum immunoprecipitation of protein complexes containing these subunits does not necessarily indicate that patients' antibodies recognize the VGKC channels, as our data shows.

The phenotype of patients with limbic encephalitis and LGI1 antibodies is different from that of patients with ADPEAF or ADLTE. This is not surprising given that some of these mutations alter the postnatal maturation of pre- and postsynaptic functions, including glutamatergic circuits, as shown in an animal model. In contrast, antibodies to LGI1 develop as part of a subacute immune response in patients without clinical or family history of ADPEAF or ADLTE, and therefore have normal glutamatergic circuits. Antibody-mediated disruption of LGI1 function may cause increased excitability resulting in seizures and other symptoms of limbic encephalopathy. These auto-antibodies may also alter the function of proteins associated with LGI1, such as ADAM22 and ADAM23, resulting in a phenotype different from that caused by mutations of LGI1.

Our findings modify several terms and concepts and will lead to a re-classification of autoimmune disorders related to VGKC. First, the term "limbic encephalitis associated with VGKC antibodies" should be changed for "limbic encephalitis associated with LGI1 antibodies". Second, the concept of "autoimmune channelopathy" needs to be reconsidered since LGI1 is not an ion channel but a secreted protein. This disorder may have to be included in the "autoimmune synaptic encephalopathies" such as those associated with NMDA or AMPA receptor antibodies. Third, it is unclear at this time whether there is any disorder associated with VGKC antibodies since a recent study implied that the antibodies of patients with Morvan's syndrome or neuromyotonia are instead directed against CASPR2, a protein member of the neurexin superfamily. In myelinated axons, CASPR2 co-localizes with Kv1.1, Kv1.2, and ADAM22, and forms part of a scaffold that is necessary to maintain VGKC at the juxtaparanodal region. CASPR2 is also expressed in hippocampal neurons, and homozygous mutations have been reported in Amish children with intractable seizures, hyperactivity, and abnormal behavior. This phenotype resembles that of the patient whose serum was used to precipitate CASPR2. In contrast, we have not identified CASPR2 antibodies in most patients with neuromyotonia or in patients with limbic encephalitis and LGI1 antibodies.

The current study clearly shows that LGI1 is the autoantigen of limbic encephalitis previously attributed to VGKC.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method of diagnosing limbic encephalitis in a subject with limbic encephalitis, comprising the steps of obtaining a serum or cerebrospinal fluid (CSF) sample from said subject; and testing said sample to determine whether an antibody to leucine-rich glioma inactivated 1 (LGI1) is present, wherein the presence of said antibody in said sample indicates said limbic encephalitis is an anti-LGI1 encephalitis, wherein the step of testing comprises an immunoassay to detect said antibody, and wherein the immunoassay comprises the steps of:
   (i) contacting the serum or CSF sample with cells that express LGI1, wherein said cells further express ADAM22 or ADAM23; and
   (ii) detecting whether a complex of LGI1 and an antibody to LGI1 is formed.

2. A method of diagnosing limbic encephalitis in a subject with limbic encephalitis, comprising the steps of obtaining a serum or cerebrospinal fluid (CSF) sample from said subject; and testing said sample to determine whether an antibody to leucine-rich glioma inactivated 1 (LGI1) is present, wherein the presence of said antibody in said sample indicates said limbic encephalitis is an anti-LGI1 encephalitis, wherein the step of testing comprises an immunoassay to detect said antibody, and wherein the immunoassay comprises the steps of:
   (i) contacting the serum or CSF sample with cells that express LGI1, wherein said cells have been treated with Brefeldin A; and
   (ii) detecting whether a complex of LGI1 and an antibody to LGI1 is formed.

3. A method of determining a cause of a limbic encephalitis in a subject with limbic encephalitis, comprising the steps of obtaining a serum or cerebrospinal fluid (CSF) sample from said subject; and testing said sample to determine whether an antibody to leucine-rich glioma inactivated 1 (LGI1) is present, wherein the step of testing comprises an immunoassay to detect said antibody, wherein the presence of said antibody in said sample indicates that LGI1 is an autoantigen of said limbic encephalitis in said subject, and wherein the immunoassay comprises the steps of:
   (i) contacting the serum or CSF sample with cells that express LGI1, wherein said cells further express ADAM22 or ADAM23; and (ii) detecting whether a complex of LGI1 and an antibody to LGI1 is formed.

4. A method of determining a cause of a limbic encephalitis in a subject with limbic encephalitis, comprising the steps of obtaining a serum or cerebrospinal fluid (CSF) sample from said subject; and testing said sample to determine whether an antibody to leucine-rich glioma inactivated 1 (LGI1) is present, wherein the step of testing comprises an immunoassay to detect said antibody, wherein the presence of said antibody in said sample indicates that LGI1 is an autoantigen of said limbic encephalitis in said subject, and wherein the immunoassay comprises the steps of:
- (i) contacting the serum or CSF sample with cells that express LGI1, wherein said cells have been treated with Brefeldin A; and
- (ii) detecting whether a complex of LGI1 and an antibody to LGI1 is formed.

* * * * *